(12) United States Patent
Botstein et al.

(10) Patent No.: US 6,472,585 B1
(45) Date of Patent: Oct. 29, 2002

(54) CARDIOTROPHIN-1 DEFECTIVE MOUSE

(75) Inventors: David Botstein, Belmont; Audrey Goddard; David A. Lawrence, both of San Francisco; Diane Pennica, Burlingame; Margaret Ann Roy, San Francisco; William I. Wood, Hillsborough, all of CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

(21) Appl. No.: 09/648,183

(22) Filed: Aug. 25, 2000

Related U.S. Application Data

(63) Continuation of application No. 09/234,730, filed on Jan. 21, 1999, now abandoned, which is a continuation of application No. 09/033,114, filed on Mar. 2, 1998, now abandoned, which is a continuation of application No. 08/733,850, filed on Oct. 18, 1996, now abandoned, which is a continuation of application No. 08/443,129, filed on May 17, 1995, now Pat. No. 5,627,073, which is a division of application No. 08/286,304, filed on Aug. 5, 1994, now Pat. No. 5,571,893, which is a continuation-in-part of application No. 08/233,609, filed on Apr. 25, 1994, now Pat. No. 5,534,615.

(60) Provisional application No. 60/113,296, filed on Dec. 22, 1998.

(51) Int. Cl.$^7$ .................... A01K 67/027; C12N 15/00; G01N 33/00
(52) U.S. Cl. ................ 800/18; 800/21; 800/3
(58) Field of Search .................. 800/3, 21, 18

(56) References Cited

U.S. PATENT DOCUMENTS

| | | | |
|---|---|---|---|
| 4,339,441 A | 7/1982 | Kalman et al. | 424/177 |
| 4,900,811 A | 2/1990 | Sutcliffe | 530/324 |
| 4,923,696 A | 5/1990 | Appel et al. | 435/29 |
| 5,017,375 A | 5/1991 | Appel et al. | 424/570 |
| 5,141,856 A | 8/1992 | Collins et al. | 435/69.1 |
| 5,166,317 A | 11/1992 | Wallace et al. | 530/350 |
| 5,202,428 A | 4/1993 | Schubert | 435/320.1 |
| 5,206,007 A | 4/1993 | Ooshima et al. | 424/9 |
| 5,210,026 A | 5/1993 | Kovesdi et al. | 435/69.1 |
| 5,214,031 A | 5/1993 | Uchida | 514/12 |
| 5,215,969 A | 6/1993 | Springer et al. | 514/21 |
| 5,218,094 A | 6/1993 | della Valle | 530/417 |
| 5,242,798 A | 9/1993 | Sutcliffe | 435/7.1 |
| 5,250,414 A | 10/1993 | Schwab et al. | 435/7.72 |
| 5,284,932 A | 2/1994 | Sen | 530/324 |
| 5,534,615 A * | 7/1996 | Baker et al. | 530/350 |
| 5,545,806 A | 8/1996 | Lonberg et al. | 800/2 |
| 5,545,807 A | 8/1996 | Surani et al. | 800/2 |
| 5,569,825 A | 10/1996 | Lonberg et al. | 800/2 |
| 5,571,675 A | 11/1996 | Baker et al. | 435/6 |
| 5,571,893 A | 11/1996 | Baker et al. | 530/350 |
| 5,624,806 A | 4/1997 | Baker et al. | 435/7.1 |
| 5,625,126 A | 4/1997 | Lonberg et al. | 800/2 |
| 5,627,073 A | 5/1997 | Baker et al. | 435/331 |
| 5,633,425 A | 5/1997 | Lonberg et al. | 800/2 |
| 5,661,016 A | 8/1997 | Lonberg et al. | 435/172.3 |
| 5,679,545 A | 10/1997 | Baker et al. | 435/69.1 |

FOREIGN PATENT DOCUMENTS

| | | |
|---|---|---|
| EP | 233838 | 8/1987 |
| EP | 474979 | 3/1992 |
| EP | 476933 | 3/1992 |
| JP | 55-020721 A | 2/1980 |
| JP | 4169600 A | 6/1992 |
| WO | WO 90/09399 | 8/1990 |
| WO | WO 92/11026 | 7/1992 |
| WO | WO 92/18140 | 10/1992 |
| WO | WO 92/20797 | 11/1992 |
| WO | WO 92/22665 | 12/1992 |
| WO | WO 93/03758 | 3/1993 |
| WO | WO 93/06116 | 4/1993 |
| WO | WO 93/07270 | 4/1993 |
| WO | WO 93/18065 | 9/1993 |
| WO | WO 93/18186 | 9/1993 |
| WO | WO 93/24529 | 12/1993 |
| WO | WO 94/05788 | 3/1994 |
| WO | WO 97/30146 | 8/1997 |
| WO | WO 99/00415 | 1/1999 |

OTHER PUBLICATIONS

Bradley et al., Modifying the mouse: Design and desire, May 1992, Bio Technology, vol. 10 pp. 534–539.*

Mullins et al., Perspective series: Molecular medicine in genetically engineered animals, 1996, Transgenic in Non–murine Species, vol., 98 No. 11 pp. 37–40.*

Fassler et al., Knockout mice: How to make them and why. The immunological approach, 1995, Int. Arch Allergy Immunol, vol. 106 pp. 323–334.*

Acland et al., "Subcellular fate of the Int–2 oncoprotein is determined by choice of initiation codon" *Nature* 343:662–665 (1990).

Alitalo and Schwab, "Oncogene amplification in tumor cells" *Advances in Cancer Research* 47:235–281 (1986).

Bazan, J.F., "Neuropoietic Cytokines in the Hematopoietic Fold" *Neuron* 7:197–208 (Aug. 1991).

Boheler et al., "Gene Expression in Cardiac Hypertrophy" *TCM* 2(5):176–182 (1992).

(List continued on next page.)

*Primary Examiner*—Deborah J. Reynolds
*Assistant Examiner*—Eleanor Sorbello
(74) *Attorney, Agent, or Firm*—Genentech, Inc.

(57) ABSTRACT

The invention concerns compositions and methods for the diagnosis and treatment of neoplastic cell growth and proliferation in mammals, including humans. The invention is based on the identification of cardiotrophin-1 gene amplified in the genome of tumor cells. Such gene amplification is expected to be associated with the overexpression of the gene product and contribute to tumorigenesis. Accordingly, the cardiotrophin-1 polypeptide encoded by the amplified gene is believed to be a useful target for the diagnosis and/or treatment (including prevention) of certain cancers, and may act as a predictor of the prognosis of tumor treatment.

2 Claims, 13 Drawing Sheets

OTHER PUBLICATIONS

Burgess et al., "Possible Dissociation of the Heparin–binding and Mitogenic Activities of Heparin–binding (Acidic Fibroblast) Growth Factor–1 from Its Receptor–binding Activities by Site–directed Mutagenesis of a Single Lysine Residue" *Journal of Cell Biology* 111:2129–2138 (1990).

Chen et al., "Pharmacological Characterization of the Activity of Endogenous Inotropic Factor from Porcine Left Ventricle" *J. Cardiovas. Pharmacol.* 22(Suppl. 2):S93–S95 (1993).

Chien et al., "Regulation of Cardiac Gene Expression During Myocardial Growth and Hypertrophy: Molecular Studies of an Adaptive Physiologic Response" *FASEB Journal* 5:3037–3046 (1991).

Chien et al., "Transcriptional Regulation During Cardiac Growth and Development" *Annu. Rev. Physiol.* 55:77–95 (1993).

Chien, K.R., "Molecular Advances in Cardiovascular Biology" *Science* 260(5110):916–917 (May 14, 1993).

Davis et al., "The Molecular Biology of the CNTF Receptor" *Current Opinion in Cell Biology* 5:281–285 (1993).

Fishwild et al., "High–avidity human IgGk monoclonal antibodies from a novel strain of minilocus transgenic mice" *Nature Biotechnology* 14(7):845–851 (Jul. 1996).

Frelin, "Serum Growth Factors for Rat Cardiac Non–Muscle Cells in Culture" *J. Molec. and Cell. Cardiol.* 12:1329–1340 (1980).

Gelmini et al., "Quantitative polymerase chain reaction–based homogeneous assay with fluorogenic probes to measure c–erbB–2 oncogene amplification" *Clinical Chemistry* 43(5):752–758 (May 1997).

Gray et al., "Fluorescence in situ hybridization in cancer and radiation biology" *Radiation Research* 137(3):275–289 (Mar. 1994).

Grimm et al., "Ventricular Nucleic Acid and Protein Levels with Myocardial Growth and Hypertrophy" *Circ. Res.* XIX:552–558 (1966).

Iwaki tkb et al., "α– and β–Adrenergic Stimulation Induces Distinct Patterns of Immediate Early Gene Expression in Neonatal Rat Myocardial Cells" *Journal of Biological Chemistry* 265(23):13809–13817 (Aug. 15, 1990).

Jones et al., "Association Between Inhibition of Arachidonic Acid Release and Prevention of Calcium Loading During ATP Depletion in Cultured Rat Cardiac Myocytes" *American Journal of Pathology* 135(3):541–556 (1989).

Kanda et al., "An Interleukin–6 Secreting Myxoma in a Hypertrophic Left Ventricle" *Chest* 105(3):962–963 (1994).

Karasik et al, "Growth Factors Identified in Myocardium of Patients with Hypertrophic Cardiomyopathy" *JACC* (abstract) 13(2):118A (1989).

Kishimoto et al., "Cytokine Signal Transduction" *Cell* 76:253–262 (Jan. 28, 1994).

Kitamura et al., "Multimeric Cytokine Receptors" *Trends Endocrinol. Metabol.* 5(1):8–14 (1994).

Knowlton et al., "Co–Regulation of the Atrial Natriuretic Factor and Cardiac Myosin Light Chain–2 Genes During α–Adrenergic Stimulation of Neonatal Rat Ventricular Cells" *Journal of Biological Chemistry* 266(12):7759–7768 (Apr. 25, 1991).

Knowlton et al., "The $α_{1a}$–Adrenergic Receptor Subtype Mediates Biochemical, Molecular, and Morphologic Features of Cultured Myocardial Cell Hypertrophy" *Journal of Biological Chemistry* 268(21):15374–15380 (Jul. 25, 1993).

Lazar et al., "Transforming Growth Factor α: Mutation of Aspartic Acid 47 and Leucine 48 Results in Different Biological Activities" *Molecular & Cellular Biology* 8(3):1247–1252 (Mar. 1988).

Lee et al., "Atrial Natriuretic Factor Gene Expression in Ventricles of Rats with Spontaneous Biventricular Hypertrophy" *J. Clin. Invest.* 81:431–434 (1988).

Lee et al., "α1–Adrenergic Stimulation of Cardiac Gene Transcription in Neonatal Rat Myocardial Cells" *Journal of Biological Chemistry* 263(15):7352–7358 (1988).

Libby, P., "Long–Term Culture of Contractile Mammalian Heart Cells in a Defined Serum–Free Medium that Limits Non–Muscle Cell Proliferation" *Journal of Molecular and Cellular Cardiology* 16:803–811 (1984).

Lin et al., "Structure Function Relationships in Glucagon: Properties of Highly Purified Des–His$^1$ –, Monoido–, and [Des–Asn$^{28}$, Thr$^{29}$] (homoserine lactone$^{27}$)–glucagon" *Biochemistry* 14(8):1559–1563 (1975).

Lonberg and Huszar, "Human antibodies from transgenic mice" *International Reviews of Immunology* 13(1):65–93 (1995).

Lonberg et al., "Antigen–specific human antibodies from mice comprising four distinct genetic modifications" *Nature* 368(6474):856–859 (Apr. 28, 1994).

Long et al., "A Growth Factor for Cardiac Myocytes is Produced by Cardiac Nonmyocytes" *Cell Regulation* 2:1081–1095 (Dec. 1991).

Long et al., "Trophic Factors in Cardiac Myocytes" *J. Hyper.* 8(Suppl. 7):S219–S224 (1990).

Long et al., "β–Adrenergic Stimulation of Cardiac Non–myocytes Augments the Growth–promoting Activity of Non–myocyte Conditioned Medium" *J. Mol. Cell. Cardiol.* 25:915–925 (1993).

Long, "TGF β Isoforms Expression and Effect in Neonatal Rat Cardiac Myocytes and Non–myocytes in Culture" *Circulation* (Abstracts from the 65th Scientific Sessions) 86:I–837 (1992).

Marks et al., "By–passing immunization: building high affinity human antibodies by chain shuffling" *Bio/Technology* 10:779–783 (1992).

McCormick et al., "Myofibrillar and Nonmyofibrillar Myocardial Proteins of Copper Deficient Rats" *J. Nutr.* (Minerals and Trace Elements) 119:1683–1690 (1989).

McDonald et al., "Expression and Characterization of Recombinant Human Ciliary Neurotrophic Factor from *Escherichia coli*" *Biochimica et Biophysica Acta* 1090:70–80 (1991).

Miller–Hance et al., "In Vitro Chamber Specification During Embryonic Stem Cell Cardiogenesis. Expression of the ventricular myosin light chain–2 gene is independent of heart tube formation" *The Journal of Biological Chemistry* 268(33):25244–25252 (Nov. 25, 1993).

Mir et al., "Isolation of a Negative Inotropic Factor from Blast Cells of Patients with Leukaemic Cardiomyopathy" *Circulation* (abstract 324) 55 & 56(Suppl. III): III–86 (1977).

Mir, "Evidence for Non–Infiltrative Neoplastic Cardiomyopathy and Presence of Negative Inotropic Factor in Acute Myeloid Leukaemia: A Clinico–Experimental Study" *British Heart J.* 39(3):355 (1977).

Morrison, S., "Immunology. Success in specification" *Nature* 368(6474):812–813 (Apr. 28, 1994).

Mukherjee et al., "Effect of Myotrophic on Induction of Proto–Oncogenes, ANF and Contractile Element Transcript Levels" *Circulation* 86(4 (Suppl. I)):I–626 (1992).

Mukherjee et al., "Myotrophic Induces Early Response Genes and Enhance Cardiac Gene Expression" *Hypertension* 21(2):142–148 (1993).

Neben et al., "The Biology of Interleukin 11" *Stem Cells* 11(Suppl. 2):156–162 (1993).

Neuberger, M., "Generating high–avidity human Mabs in mice" *Nature Biotechnology* 14(7):826 (Jul. 1996).

Patterson, "The Emerging Neuropoietic Cytokine Family: Fist CDF/LIF, CNTF and IL–6; next ONC, MGF, GCSF?" *Curr. Opin. Neurobiol.* 2:94–97 (1992).

Pennica et al., "Expression cloning of cardiotrophin 1, a cytokine that induces cardiac myocyte hypertrophy" *Proc. Natl. Acad. Sci. USA* 92:1142–1146 (1995).

Pennica et al., "Human Cardiotrophin–1: Protein and Gene Structure, Biological and Binding Activities, and Chromosomal Localization" *Cytokine* 8(3):183–189 (1996).

Ramaciotti et al., "Cardiac Endothelial Cells Modulate Contractility of Rat Heart in Response to Oxygen Tension and Coronary Flow" *Circ. Res.* 72(5):1044–1064 (1993).

Robbins et al., "Mouse Embryonic Stem Cells Express the Cardiac Myosin Heavy Chain Genes During Development in Vitro" *Journal of Biological Chemistry* 265(20):11905–11909 (1990).

Rockman et al., "Segregation of Atrial–Specific and Incubile Expression of an Atrial Natriuretic Factor Transgene in an in vivo Murine Model of Cardiac Hypertrophy" *Proc. Natl. Acad. Sci. USA* 88:8277–8281 (Sep. 1991).

Sadoshima et al., "Autocrine Release of Angiotensin II Mediates Stretch–Induced Hypertrophy of Cardiac Myocytes in Vitro" *Cell* 75:977–984 (1993).

Sarzani et al., "Regulation of Cardiac Growth Factors and Growth Factor Receptors Gene Expression by Growth Hormone" *European Heart Journal* (abst. suppl.) 13:326 (1992).

Schwab and Amler, "Amplification of cellular oncogenes: a predictor of clinical outcome in human cancer" *Genes, Chromosome & Cancer* 1(3):181–193 (Jan. 1990).

Schwartz et al., "A superactive insulin: [B10–Aspartic acid] insulin(human)" *Proc. Natl. Acad. Sci. USA* 84:6408–6411 (Sep. 1987).

Seaver, "Monoclonal Antibodies in Industry: More Difficult Than Originally Tought" *Genetic Engineering News* Aug. 1994:10 and 21 (1994).

Sen et al., "Basic Science/Circulation: Myocardial Structure and Pathology–Hypertrophy" *Circulation* 80(4 (Suppl. II)):II–616 (1989).

Sen et al., "Myotrophin: Purification of a Novel Peptide from Spontaneously Hypertensive Rat Heart That Influences Myocardial Growth" *Journal of Biological Chemistry* 265(27):16635–16643 (1990).

Shubeita et al., "Endothelin Induction of Inositol Phospholipid Hydrolysis, Sarcomere Assembly, and Cardiac Gene Expression in Ventricular Myocytes. A paracrine mechanism for myocardial cell hypertrophy" *Journal of Biological Chemistry* 265(33):20555–20562 (Nov. 25, 1990).

Sil et al., "Myotrophin in Human Cardiomyopathic Heart" *Circ. Res.* 73(1):98–108 (1993).

Sil et al., "Purification of Myotrophin from Human Cardiomyopathic Heart" *FASEB J.* 5(5991):A1244 (1991).

Sil et al., "Role of Myotrophic in Pathophysiology of Cardiac Hypertrophy in Spontaneously Hypertensive Rat (SHR)" *Circulation* 88(4, part 3):I–613 (1993).

Simpson et al., "Differentiation of Rat Myocytes in Single Cell Cultures with and without Proliferating Nonmyocardial Cells. Cross–striations, ultrastructure, and chronotropic response to isoproterenol" *Circulation Research* 50(1):101–116 (Jan. 1982).

Simpson et al., "Myocyte Hypertrophy in Neonatal Rat Heart Cultures and Its Regulation by Serum and by Catecholamines" *Circulation Research* 51(6):787–801 (Dec. 1982).

Suzuki et al., "Serum–Free, Chemically Defined Medium is Important to Investigate the Growth, Development and Function of Neonatal Rat Cardiac Myocytes in Culture" *Trends in Animal Cell Culture Technology*, Murakami (ed.), Tokyo:Kodansha pp. 61–66 (1990).

Takemura et al., "Expression and Distribution of Atrial Natriuretic Peptide in Human Hypertrophic Ventricle of Hypertensive Hearts and Hearts with Hypertrophic Cardiomyopathy" *Circulation* 83(1):181–190 (1991).

Williams et al., "Cardiovascular Growth Factors" *The Heart and Cardiovascular System*, Fozzard et al. (eds.), New York:Raven Press, Chapter 72, pp. 1 (1986).

\* cited by examiner

FIG. 1A

```
 901 AGCTGGGACT ACAGGCACGC GCCACCACAG CCGGCTAATT TTTTATTTAA TTTTTTGTAG AGACGAGGTT TCGCCATGTT GCCCAGGCTG GTCTTGAACT
     TCGACCCTGA TGTCCGTGCG CGGTGGTGTC GGCCGATTAA AAAATAAATT AAAAACATC TCTGCTCCAA AGCGGTACAA CGGGTCCGAC CAGAACTTGA

1001 CCGGGGCTCA AGCGATCCTC CCGCTTCAGC CTCCCTAAGT GCTGGGATTG CAGGCGTGAG CCACTTCCCC AGCCTCTCTT TGCTTTGCCT GCCCCGTTCT
     GGCCCCGAGT TCGCTAGGAG GGCGAAGTCG GAGGGATTCA CGACCCTAAC GTCCGCACTC GGTGAAGGG TCGGAGAGAA ACGAAACGGA CGGGGCAAGA
                                                                                        ^58125.tm.f1

1101 CTTAACTCTT GGACCCTCCT CGTCTGCATG GTAACTCCGT CTGAGTCTAC CATTTTCTTG CTCTCCCTCC TTCCTTGGGC CTGCCTCAGT TCCCTTGGC
     GAATTGAGAA CCTGGGAGGA GCAGACGTAC CATTGAGGCA GACTCAGATG GTAAAAGAAC GAGAGGGAGG AAGGAACCCG GACGGAGTCA AGGGAACCG
                                               ^58125.tm.r1

1201 CTCCCCCTTT ACCCAGCTCT TGGGGTGTCT CTGTTTTTTC CATCCCCAGT TCCTGCCCTC TGTGGCCCT GTGTGAGCAC ATGTGTACAT CTCAGCCTTA
     GAGGGGGAAA TGGGTCGAGA ACCCCACAGA GACAAAAAAG GTAGGGGTGA AGGACGGAAG AGCACCGGGA CACACTCGTG TACACATGTA GAGTCGGAAT

1301 TCTCAAGGAG GTGACACCTT CTCTCCTTCT CCCCATCTGG CCGTCTCTCT GTGCTTCCCT GGCCAGGGGC GTGCCTGCTG GTCCTATGGG GGGAAGGCTA
     AGAGTTCCTC CACTGTGGAA GAGAGGAAGA GGGGTAGACC GGCAGAGAGA CACGAAGGGA CCGGTCCCCG CACGGACGAC CAGGATACCC CCCTTCCGAT

1401 CTCCGCATCT CAGCCACCTC CCTCAGGCTC ACTCCACCTA CTGCCACACC CTGTCCCAGC CCTGTCCCTT GGGCCTCAGC CCTGTCCCTT TGATGTCCTC
     GAGGCGTAGA GTCGGTGGAG GGAGTCCGAG TGAGGTGGAT GACGGTGTGG GACAGGGTCG GGACAGGGAA CCCGGAGTCG GGACAGGGAA ACTACAGGAG

1501 CTTTCCTTCA GCCCCCTCTGC CCTGTCCCTG CACACCTCC (SEQ ID NO:1)
     GAAAGGAAGT CGGGGAGACG GGACAGGGAC GTGTGGAGG (SEQ ID NO:2)
```

FIG. 1B

Framework Analysis of DNA58125 Cardiotrophin-1 on Lung Tumor Panel 1

Framework Analysis of DNA58125 Cardiotrophin-1 on Lung Tumor Panel 2

Framework Analysis of DNA58125 Cardiotrophin-1 on Colon Tumor Panel #1

CARDIOTROPHIN-1 DEFECTIVE MOUSE

CROSS-REFERENCE TO RELATED APPLICATIONS

This is a non-provisional continuation application filed under 37 C.F.R. 1.53(b) (1), claiming priority under 35 U.S.C. 120 to U.S. Application Ser. No. 09/234,730 filed Jan. 21, 1999, now abandoned, which is a continuation U.S. Application Ser. No. 09/033,114 filed Mar. 2, 1998, abandoned, which is a continuation of U.S. Application Ser. No. 08/733,850 filed Oct. 18, 1996, now abandoned, which is a continuation of U.S. Application Ser. No. 08/443,129 filed May 17, 1995, issued May 6, 1997 as U.S. Pat. No. 5,627,073, which is a divisional application of 08/286,304 filed Aug. 5, 1994, issued Nov. 5, 1996 as U.S. Pat. No. 5,571,893, which is a continuation-in-part of U.S. Application Ser. No. 08/233,609 filed Apr. 25, 1994, issued Jul. 9, 1996 as U.S. Pat. No. 5,534,615, and to U.S. Application Ser. No. 60/113,296, filed Dec. 22, 1998, now abandoned, which applications are herein incorporated by reference in their entirety.

FIELD OF THE INVENTION

The present invention relates to compositions and methods for the diagnosis and treatment of tumor.

BACKGROUND OF THE INVENTION

Malignant tumors (cancers) are the second leading cause of death in the United States, after heart disease (Boring et al., *CA Cancel J. Clin.* 43, 7,[1993]).

Cancer is characterized by the increase in the number of abnormal, or neoplastic, cells derived from a normal tissue which proliferate to form a tumor mass, the invasion of adjacent tissues by these neoplastic tumor cells, and the generation of malignant cells which eventually spread via the blood or lymphatic system to regional lymph nodes and to distant sites (metastasis). In a cancerous state a cell proliferates under conditions in which normal cells would not grow. Cancer manifests itself in a wide variety of forms, characterized by different degrees of invasiveness and aggressiveness.

Alteration of gene expression is intimately related to the uncontrolled cell growth and de-differentiation which are a common feature of all cancers. The genomes of certain welt studied tumors have been found to show decreased expression of recessive genes, usually referred to as tumor suppression genes, which would normally function to prevent malignant cell growth, and/or overexpression of certain dominant genes, such as oncogenes, that act to promote malignant growth. Each of these genetic changes appears to be responsible for importing some of the traits that, in aggregate, represent the full neoplastic phenotype (Hunter, *Cell* 64, 1129 [1991]; Bishop, *Cell* 64, 235–248 [1991]).

A well known mechanism of gene (e.g. oncogene) overexpression in cancer cells is gene amplification. This is a process where in the chromosome of the ancestral cell multiple copies of a particular gene are produced. The process involves unscheduled replication of the region of chromosome comprising the gene, followed by recombination of the replicated segments back into the chromosome (Alitalo et al., *Adv. Cancer Res.* 47, 235–281 [1986]). It is believed that the overexpression of the gene parallels gene amplification, i.e. is proportionate to the number of copies made.

Proto-oncogenes that encode growth factors and growth factor receptors have been identified to play important roles in the pathogenesis of various human malignancies, including breast cancer. For example, it has been found that (he human ErbB2 gene (erbB2, also known as her2, or c-erbB-2), which encodes a 185-kd transmembrane glycoprotein receptor (p185$^{HER2}$; HER2) related to the epidermal growth factor receptor (EGFR), is overexpressed in about 25% to 30% of human breast cancer (Slamon et al., *Science* 235:177–182 [1987]; Slamon et al., *Science* 244:707–712 [1989]).

It has been reported that gene amplification of a protooncogen is an event typically involved in the more malignant forms of cancer, and could act as a predictor of clinical outcome (Schwab et al., *Genes Chromosomes Cancer* 1, 181–193 [1990]; Alitalo et al., supra). Thus, erbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19–27 [1995]; and Hynes and Stern, *Biochim Biophys Acta* 1198:165–184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11(3 Suppl 1):43–48 [1997]). However, despite the association of erbB2 overexpression with poor prognosis, the odds of HER2-positive patients responding clinically to treatment with taxanes were greater than three times those of HER2-negative patients (Ibid). A recombinant humanized anti-ErbB2 (anti-HER2) monoclonal antibody (a humanized version of the murine anti-ErbB2 antibody 4D5, referred to as rhuMAb HER2 or Herceptin®) has been clinically active in patients with ErbB2-overexpressing metastatic breast cancers that had received extensive prior anticancer therapy. (Baselga et al., *J. Clin. Oncol.* 14:737–744 [1996]).

SUMMARY OF THE INVENTION

The present invention concerns compositions and methods for the diagnosis and treatment of neoplastic cell growth and proliferation in mammals, including humans. The present invention is based on the identification of a gene that are amplified in the genome of tumor cells. Such gene amplification is expected to be associated with the overexpression of the gene product and contribute to tumorigenesis. Accordingly, the protein encoded by the amplified gene is believed to be a useful target for the diagnosis and/or treatment (including prevention) of certain cancers, and may act of predictors of the prognosis of tumor treatment.

A gene product, CT-1, is useful in the treatment of heart failure and/or neurological disorders such as peripheral neuropathy was disclosed in U.S. Pat. No. 5,571,675 (herein incorporated by reference in its entirety). The surprising discovery that CT-1 is amplified in tumor cells, such as lung and colon tumor cells, is disclosed herein. Applicant's discovery that CT-1 is amplified in tumor cells led to the additional discoveries of compositions for treatment of tumor cells and methods of carrying out such treatment.

In one embodiment, the present invention concerns an isolated antibody which binds a CT-1 polypeptide. In one aspect, the antibody induces death of a cell overexpressing a CT-1 polypeptide. In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a single-chain antibody, or an anti-idiotypic antibody.

In another embodiment, the invention concerns a composition comprising an antibody which binds a CT-1 polypeptide in admixture with a pharmaceutically acceptable carrier. In one aspect, the composition comprises a therapeutically effective amount of the antibody. In another aspect, the composition comprises a further active ingredient, which may, for example, be a further antibody or a cytotoxic or chemotherapeutic agent. Preferably, the composition is sterile.

In a further embodiment, the invention concerns nucleic acid encoding an anti-CT-1 antibody, and vectors and recombinant host cells comprising such nucleic acid.

In a still further embodiment, the invention concerns a method for producing an anti-CT-1 antibody by culturing a host cell transformed with nucleic acid encoding the antibody under conditions such that the antibody is expressed, and recovering the antibody from the cell culture.

The invention further concerns antagonists and agonists of a CT-1 polypeptide that inhibit one or more of the functions or activities of the CT-1 polypeptide.

In another embodiment, the invention concerns a method for determining the presence of a CT-1 polypeptide comprising exposing a cell suspected of containing the CT-1 polypeptide to an anti-CT-1 antibody and determining binding of the antibody to the cell.

In yet another embodiment, the present invention concerns a method of diagnosing tumor in a mammal, comprising detecting the level of expression of a gene encoding a CT-1 polypeptide (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained.

In another embodiment, the present invention concerns a method of diagnosing tumor in a mammal, comprising (a) contacting an anti-CT-1 antibody with a test sample of tissue cells obtained from the mammal, and (b) detecting the formation of a complex between the anti-CT-1 antibody and the CT-1 polypeptide in the test sample. The detection may be qualitative or quantitative, and may be performed in comparison with monitoring the complex formation in a control sample of known normal tissue cells of the same cell type. A larger quantity of complexes formed in the test sample indicates the presence of tumor in the mammal from which the test tissue cells were obtained. The antibody preferably carries a detectable label. Complex formation can be monitored, for example, by light microscopy, flow cytometry, fluorimetry, or other techniques known in the art.

The test sample is usually obtained from an individual suspected to have neoplastic cell growth or proliferation (e.g. cancerous cells).

In another embodiment, the present invention concerns a cancer diagnostic kit, comprising an anti-CT-1 antibody and a carrier (e.g. a buffer) in suitable packaging. The kit preferably contains instructions for using the antibody to detect the CT-1 polypeptide.

In yet another embodiment, the invention concerns a method for inhibiting the growth of tumor cells comprising exposing a cell which overexpresses a CT-1 polypeptide to an effective amount of an agent inhibiting the expression and/or activity of the CT-1 polypeptide. The agent preferably is an anti-CT-1 antibody, a small organic and inorganic molecule, peptide, phosphopeptide, antisense or ribozyme molecule, or a triple helix molecule. In a specific aspect, the agent, e.g. anti-CT-1 antibody induces cell death. In a further aspect, the tumor cells are further exposed to radiation treatment and/or a cytotoxic or chemotherapeutic agent.

In a further embodiment, the invention concerns an article of manufacture, comprising:

a container;

a label on the container; and a composition comprising an active agent contained within the container; wherein the composition is effective for inhibiting the growth of tumor cells, the label on the container indicates that the composition can be used for treating conditions characterized by overexpression of a CT-1 polypeptide, and the active agent in the composition is an agent inhibiting the expression and/or activity of the CT-1 polypeptide. In a preferred aspect, the active agent is an anti-CT-1 antibody.

A method for identifying a compound capable of inhibiting the expression and/or activity of a CT-1 polypeptide, comprising contacting a candidate compound with a CT-1 polypeptide under conditions and for a time sufficient to allow these two components to interact. In a specific aspect, either the candidate compound or the CT-1 polypeptide is immobilized on a solid support. In another aspect, the non-immobilized component carries a detectable label.

BRIEF DESCRIPTION OF THE DRAWINGS

Figure 1A:
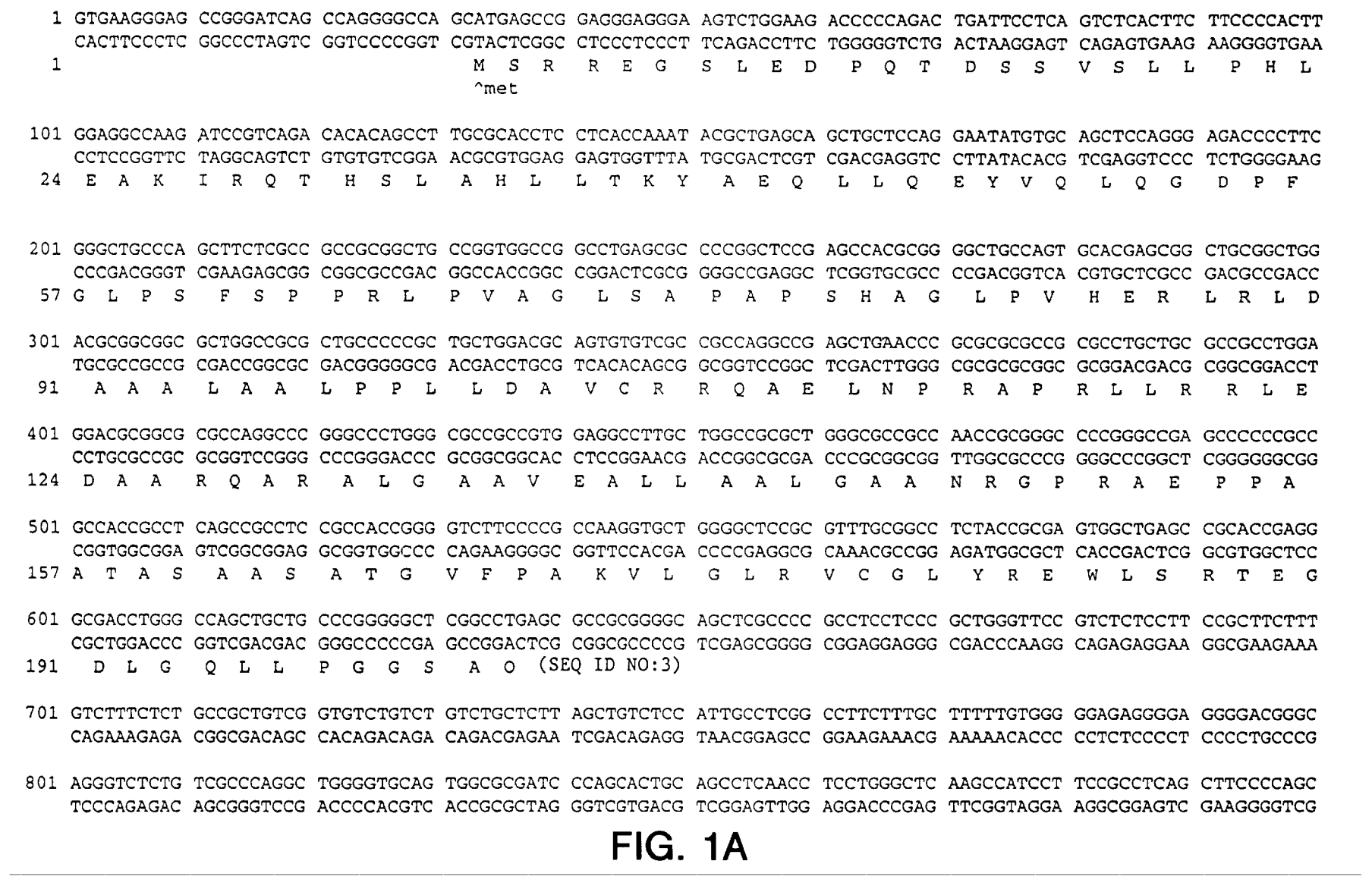

FIGS. 1A and 1B (SEQ ID NO: 1 and 2) show the nucleotide sequence of DNA58125 that is a cDNA encoding a native sequence cardiotrophin-1 (CT-1 ). SEQ ID NO:1 is the coding strand of DNA58125 and SEQ ID NO:2 is the complementary strand of DNA58125. FIG. 1A SEQ ID NO:3 shows, the derived amino acid sequence of a native sequence cardiotrophin-1 (CT-1 ).

DETAILED DESCRIPTION OF THE INVENTION

I. Definitions

Figure 2:
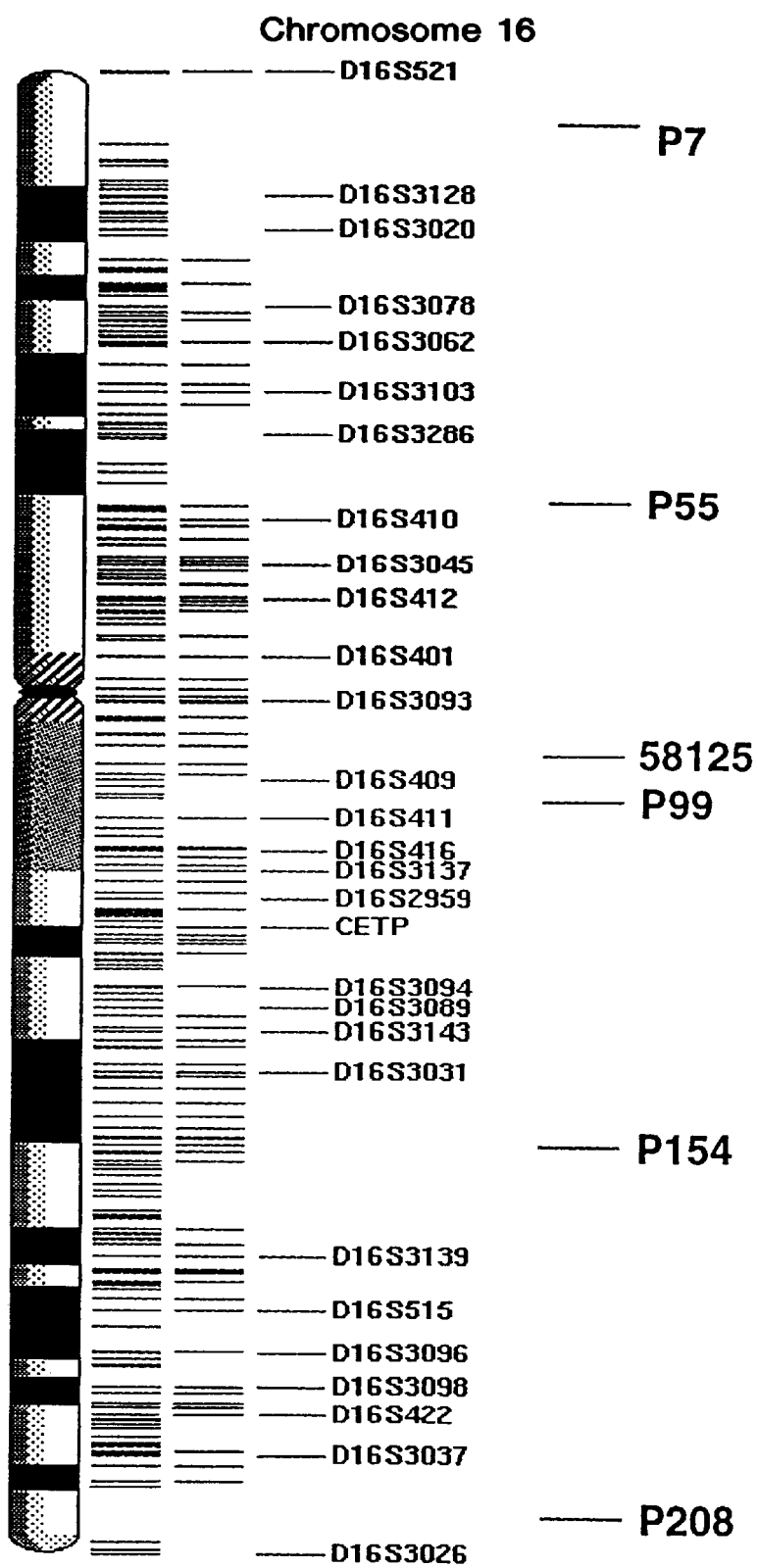
FIG. 2 is a diagram of human chromosome 16 indicating the regions of the chromosome at which DNA58125 and various marker probes hybridize. The marker probes (P7, P55, P99, P154, and P208) are located approximately every 20 Megabases along chromosome 16 and are used as controls for measurement of genetic amplification. DNA58125 hybridizes to a region on the long arm between the centromere and marker probe P99.

The phrases "gene amplification" and "gene duplication" are used interchangeably and refer to a process by which multiplie copies of a gene or gene fragment are formed in a particular cell or cell line. The duplicated region (a stretch of amplified DNA) is often referred to as "amplicon." Usually, the amount of the messenger RNA (mRNA) produced, i.e. the level of gene expression, also increases in the proportion of the number of copies made of the particular gene expressed.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, inannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol, Bristol-Myers Squibb Oncology, Princeton, N.J.), and doxetaxel (Taxotere, Rhône-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase of the cell cycle. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et at. (W B Saunders: Philadelphia, 1995), especially p. 13.

"Doxorubicin" is an athracycline antibiotic. The full chemical name of doxorubicin is (8S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL4, IL-5, IL-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the terms a "CT-1" polypeptide is used to refer to a polypeptide comprising a native sequence polypeptide having the same amino acid sequence as a corresponding CT-1 polypeptide derived from nature, and fragments of such native sequence polypeptides. Such native sequence CT-1 polypeptides can be isolated from nature or, along with the respective fragments, can be produced by recombinant and/or synthetic means. The term specifically encompasses naturally-occurring truncated or secreted forms (e.g., an extracellular domain sequence), naturally-occurring variant forms (e.g., alternatively spliced forms) and naturally-occurring allelic variants of the CT-1 polypeptide. In one embodiment of the invention, the native sequence CT-1 is a full-length native presequence or a mature form of a CT-1 polypeptide shown in FIG. 1A (SEQ ID NO:3). Fragments of the respective native polypeptides herein include, but are not limited to, polypeptide variants from which the native N-terminal signal sequence has been fully or partially deleted or replaced by another sequence, and extracellular domains of the respective native sequences, regardless whether such truncated (secreted) forms occur in nature.

An "isolated" nucleic acid molecule encoding a CT-1 polypeptide is a nucleic acid molecule that is identified and separated from at least one contaminant nucleic acid molecule with which it is ordinarily associated in the natural source of the CT-1-encoding nucleic acid. An isolated CT-1-encoding nucleic acid molecule is other than in the form or setting in which it is found in nature. Isolated nucleic acid molecules therefore are distinguished from the CT-1-encoding nucleic acid molecule as it exists in natural cells. However, an isolated nucleic acid molecule encoding a CT-1 polypeptide includes nucleic acid molecules contained in cells that ordinarily express CT-1, where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment low their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50mM sodium phosphate buffer at pH 6.5 with 750 mM sodium chloride, 75 mM sodium citrate at 42° C; or (3) employ formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent than those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a CT-1 polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

"Active" or "activity" in the context of molecules identified based upon the CT-1 polypeptides (or their coding sequences) refers to polypeptides (e.g. antibodies) or organic or inorganic small molecules, peptides, etc. which retain the biological and/or immunological activities/properties of a native or naturally-occurring CT-1.

"Biological activity" in the context of an antibody or another molecule that can be identified by the screening assays disclosed herein (e.g. an organic or inorganic small molecule, peptide, etc.) is used to refer to the ability of such molecules to bind or complex with the polypeptides encoded by the amplified genes identified herein, or otherwise interfere with the interaction of the encoded polypeptides with other cellular proteins. A preferred biological activity is growth inhibition of a target tumor cell. Another preferred biological activity is cytotoxic activity resulting in the death of the target tumor cell.

The phrase "immunological property" means immunological cross-reactivity with at least one epitope of a CT-1 polypeptide.

"Immunological cross-reactivity" as used herein means that the candidate polypeptide is capable of competitively inhibiting the qualitative biological activity of a CT-1 polypeptide having this activity with polyclonal antisera raised against the known active CT-1 polypeptide. Such antisera are prepared in conventional fashion by injecting goats or rabbits, for example, subcutaneously with the known active analogue in complete Freund's adjuvant, followed by booster intraperitoneal or subcutaneous injection in incomplete Freunds. The immunological cross-reactivity preferably is "specific", which means that the binding affinity of the immunologically cross-reactive molecule (e.g. antibody) identified, to the corresponding CT-1 polypeptide is significantly higher (preferably at least about 2-times, more preferably at least about 4-times, even more preferably at least about 8-times, most preferably at least about 8-times higher) than the binding affinity of that molecule to any other known native polypeptide.

The term "antagonist" is used in the broadest sense, and includes any molecule that partially or fully blocks, inhibits, or neutralizes a biological activity of a native CT-1 polypeptide disclosed herein. In a similar manner, the term "agonist" is used in the broadest sense and includes any molecule that mimics a biological activity of a native CT-1 polypeptide disclosed herein. Suitable agonist or antagonist molecules specifically include agonist or antagonist antibodies or antibody fragments, fragments or amino acid sequence variants of native polypeptides, peptides, small organic molecules, etc.

A "small molecule" is defined herein to have a molecular weight below about 500 daltons.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas. The term "antibody" is used in the broadest sense and specifically covers, without limitation, intact monoclonal antibodies, polyclonal antibodies, multispecific antibodies (e.g. bispecific antibodies) formed from at least two intact antibodies, and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *NIH Publ. No.*91–3242, Vol. I, pages 647–669 (1991)). The constant domains are not involved directly in binding an antibody to an antigen, but exhibit various effector functions, such as participation of the antibody in antibody-dependent cellular toxicity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al., *Protein Eng.* 8(10):1057–1062 [1995]); single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab fragments by the addition of a few residues at the carboxy terminus of the heavy chain CH1 domain including one or more cysteines from the antibody hinge region. Fab'-SH is the designation herein for Fab'0 in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 [1975], or may be made by recombinant DNA methods (see, e.g., U.S. Pat. No. 4,816,567). The "monoclonal antibodies" may also be isolated from phage antibody libraries using the techniques described in Clackson et al., *Nature*, 352:624–628 [1991] and Marks et al., *J. Mol. Biol.*, 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat. Acad. Sci. USA*, 81:6851–6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a CDR of the recipient are replaced by residues from a CDR of a non-human species (donor antibody) such as mouse, rat or rabbit having the desired specificity, affinity, and capacity. In some instances, Fv FR residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522–525 (1986); Reichmann et al., *Nature*, 332:323–329 [1988]; and Presta, *Curr. Op. Struct. Biol.*, 2:593–596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Attibodies*, vol. 113, Rosenburg and Moore eds., Springer-Verlag, New York, pp. 269–315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an CT-1 polypeptide or an antibody thereto and, optionally, a chemotherapeutic agent) to a mammal. The components of the liposome are commonly arranged in a bilayer formation, similar to the lipid arrangement of biological membranes.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

II. Compositions and Methods of the Invention

1. Preparation of the CT-1 polypeptides

The present invention provides methods for using DNA58125 encoding CT-1 for the production of compounds inhibiting neoplastic growth as well as for the preparation of screening methods for identifying growth inhibitory compounds (e.g. tumor compounds). In particular, cDNAs encoding certain CT-1 polypeptides. For the sake of simplicity, in the present specification the proteins encoded by nucleic acid referred to as "DNA58125", as well as all further native homologues and variants included in the foregoing definition of CT-1 polypeptide, will be referred to as "CT-1" polypeptide, regardless of their origin or mode of expression.

The description below relates primarily to production of CT-1 polypeptides by culturing cells transformed or transfected with a vector containing CT-1 -encoding nucleic acid. It is, of course, contemplated that alternative methods, which are well known in the art, may be employed to prepare CT-1 polypeptides. For instance, the CT-1 polypeptide sequence, or portions thereof, may be produced by direct peptide synthesis using solid-phase techniques [see, e.g., Stewart et al., *Solid-Phase Peptide Synthesis,* W. H. Freeman Co., San Francisco, Calif. (1969); Merrifield, *J. Am. Chem. Soc.,* 85:2149–2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the CT-1 polypeptide may be chemically synthesized separately and combined using chemical or enzymatic methods to produce the full-length CT-1.

i. Synthesis or Isolation of DNA Encoding a CT-1 polypeptide

DNA encoding CT-1, homologues, variants, or portions thereof, may be produced by direct DNA synthesis using standard nucleic acid synthetic techniques [see, e.g., Gait, M. J., *Oligonucleotide Synthesis,* IRL Press, Oxford, 1984]. In vitro, DNA synthesis may be performed using manual techniques or by automation. Automated oligonucleotide may be accomplished, for instance, using standard techniques. Various portions of the CT-1-encoding nucleic acid sequence may be chemically synthesized separately and combined using chemical or enzymatic methods to produce the full-length CT-1 -encoding sequence.

Alternatively, DNA encoding CT-1 may be obtained from a cDNA library prepared from tissue believed to possess the CT-1 mRNA and to express it at a detectable level. Accordingly, human CT-1 DNA can be conveniently obtained from a cDNA library prepared from human tissue, such as described in the Examples. The CT-1 -encoding gene may also be obtained from a genomic library or by oligonucleotide synthesis.

Libraries can be screened with probes (such as antibodies to the CT-1 polypeptide, or oligonucleotides of at least about 20–80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding CT-1 is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined through sequence alignment using computer software programs such as ALIGN, DNAstar, and INHERIT which employ various algorithms to measure homology.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

ii. Selection and Transformation of Host Cells

Host cells are transfected or transformed with expression or cloning vectors described herein for CT-1 production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach,* M. Butler, ed. (IRL Press, 1991) and Sambrook et al., supra.

Methods, of transfection are known to the ordinarily skilled artisan, for example, CaPO$_4$ and electroporation. Depending on the host cell used, transformation is performed using standard techniques appropriate to such cells. The calcium treatment employing calcium chloride, as described in Sambrook et al., supra, or electroporation is generally used for prokaryotes or other cells that contain substantial cell-wall barriers. Infection with Agrobacterium tumefaciens is used for transformation of certain plant cells, as described by Shaw et al., *Gene,* 23:315 (1983) and WO 89/05859 published Jun. 29, 1989. For mammalian cells without such cell walls, the calcium phosphate precipitation method of Graham and van der Eb, *Viroloy,* 52:456457 (1978) can be employed. General aspects of mammalian cell host system transformations have been described in U.S. Pat. No. 4,399,216. Transformations into yeast are typically carried out according to the method of Van Solingen et al., *J. Bact.,* 130:946 (1977) and Hsiao et al., *Proc. Natl. Acad. Sci.* (*USA*), 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology,* 185:527–537 (1990) and Mansour et al., *Nature,* 336:348–352 (1988).

Suitable host cells for cloning or expressing the DNA in the vectors herein include prokaryote, yeast, or higher eukaryote cells. Suitable prokaryotes include, but are not limited to, eubacteria, such as Gram-negative or Gram-positive organisms, for example, Enterobacteriaceae such as *E. coli.* Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic microbes such as filamentous fungi or yeast are suitable cloning or expression hosts for CT-1-encoding vectors. Saccharomyces cerevisiae is a commonly used lower eukaryotic host microorganism.

Suitable host cells for the expression of glycosylated CT-1 are derived from multicellular organisms. Examples of invertebrate cells include insect cells such as Drosophila S2 and Spodoptera Sf9, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.,* 36:59 (1977)); Chinese hamster ovary cells/-DHFR (CHO, Urlaub and Chasin, *Proc. Natl. Acad. Sci. USA,* 77:4216 (1980)); mouse sertoli cells (TM4, Mather, *Biol. Reprod.,* 23:243–251 (1980)); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

iii. Selection and Use of a Replicable Vector

The nucleic acid (e.g., cDNA or genomic DNA) encoding CT-1 may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan.

The CT-1 polypeptide may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the CT-1 -encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including Saccharomyces and Kluyveromyces α-factor leaders, the latter described in U.S. Pat. No. 5,010, 182), or acid phosphatase leader, the *C. albicans* glucoamylase leader (EP 362,179 published Apr. 4, 1990), or the signal described in WO 90/13646 published Nov. 15, 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2µplasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

An example of suitable selectable markers for mammalian cells are those that enable the identification of cells competent to take up the CT-1-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA,* 77:4216 (1980). A suitable selection gene for use in yeast is the trp 1 gene present in the yeast plasmid YRp7 [Stinchcomb et al., *Nature,* 282:39 (1979); Kingsman et al., *Gene,* 7:141 (1979); Tschemper et al., *Gene,* 10:157 (1980)]. The trp 1 gene provides a selection marker for a mutant strain of yeast lacking the ability to grow in tryptophan, for example, ATCC No. 44076 or PEP4-1 [Jones, *Genetics,* 85:12 (1977)].

Expression and cloning vectors usually contain a promoter operably linked to the CT-1 -encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature,* 275:615 (1978); Goeddel et al., *Nature,* 281:544 (1979)], alkaline phosphatase, a tryptophan (trp) promoter system [Goeddel, *Nucleic Acids Res.,* 8:4057 (1980); EP 36,7761, and hybrid promoters such as the tac promoter [deBoer et al., *Proc. Natl. Acad. Sci. USA,* 80:21–25 (1983)]. Promoters for use in bacterial systems also will contain a Shine-Dalgarno (S.D.) sequence operably linked to the DNA encoding CT-1.

Examples of suitable promoting sequences for use with yeast hosts include the promoters for 3-phosphoglycerate kinase [Hitzeman et al., *J. Biol. Chem.,* 255:2073 (1980)] or other glycolytic enzymes [Hess et al., *J. Adv. Enzyme Reg.,* 7:149 (1968); Holland, *Biochemistry,* 17:4900(1978)], such as enolase, glyceraldehyde-3phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase; and enzymes responsible for maltose and galactose utilization. Suitable vectors and promoters for use in yeast expression are further described in EP 73,657.

CT-1 transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding a CT-1 polypeptide by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the CT-1 coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding CT-1.

Still other methods, vectors, and host cells suitable for adaptation to the synthesis of CT-1 in recombinant vertebrate cell culture are described in Gething et al., *Nature* 293:620–625 (1981); Mantei et al., *Nature,* 281:4046 (1979); EP 117,060; and EP 117,058.

iv. Detecting Gene Amplification/Expression

Gene amplification and/or expression may be measured in a sample directly, for example, by conventional Southern blotting, Northern blotting to quantitate the transcription of mRNA [Thomas, *Proc. Natl. Acad. Sci. USA,* 77:5201–5205 (1980)], dot blotting (DNA analysis), or iti situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence CT-1 polypeptide or against a synthetic peptide based on the DNA sequences provided herein or against exogenous sequence fused to CT-1 DNA and encoding a specific antibody epitope.

v. Purification of Polypeptide

Forms of CT-1 polypeptides may be recovered from culture medium or from host cell lysates. If membranebound, it can be released from the membrane using a suitable detergent solution (e.g. Triton-X 100) or by enzymatic cleavage. Cells employed in expression of CT-1 can be disrupted by various physical or chemical means, such as freeze-thaw cycling, sonication, mechanical disruption, or cell lysing agents.

It may be desired to purify CT-1 from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the CT-1 polypeptides. Various methods of protein purification may be employed and such methods are known in the art and described for example in Deutscher, Methods in Enzymology, 182(1990); Scopes, Protein Purification: Principles and Practice, Springer-Verlag, New York (1982). The purification step(s) selected will depend, for example, on the nature of the production process used and the particular CT-1 polypeptide produced.

2. Amplification of Genes Encoding the CT-1 Polypeptides in Tumor Tissues and Cell Lines The present invention is based on the identification and characterization of genes which are amplified in certain cancer cells.

The genome of prokaryotic and eukaryotic organisms is subjected to two seemingly conflicting requirements. One is the preservation and propagation of DNA as the genetic information in its original form, to guarantee stable inheritance through multiple generations. On the other hand, cells or organisms must be able to adapt to lasting environmental changes. The adaptive mechanisms can include qualitative or quantitative modifications of the genetic material. Qualitative modifications include DNA mutations, in which coding sequences are altered resulting in a structurally and/or functionally different protein. Gene amplification is a quantitative modification, whereby the actual number of complete coding sequence, i.e. a gene, increases, leading to an increased number of available templates for transcription, an in creased number of translatable transcripts, and, ultimately, to an increased abundance of the protein encoded by the amplified gene.

The phenomenon of gene amplification and its underlying mechanisms have been investigated in vitro in several prokaryotic and eukaryotic culture systems. The best-characterized example of gene amplification involves the culture of eukaryotic cells in medium containing variable concentrations of the cytotoxic drug methotrexate (MTX). MTX is a folic acid analogue and interferes with DNA synthesis by blocking the enzyme dihydrofolate reductase (DHFR). During the initial exposure to low concentrations of MTX most cells (>99.9%) will die. A small number of cells survive, and are capable of growing in increasing concentrations of MTX by producing large amounts of DHFR-RNA and protein. The basis of this overproduction is the amplification of the single DHFR gene. The additional copies of the gene are found as extrachromosomal copies in the form of small, supernumerary chromosomes (double minutes) or as integrated chromosomal copies.

Gene amplification is most commonly encountered in the development of resistance to cytotoxic drugs (antibiotics for bacteria and chemotherapeutic agents for eukaryotic cells) and neoplastic transformation. Transformation of a eukaryotic cell as a spontaneous event or due to a viral or chemical/environmental insult is typically associated with changes in the genetic material of that cell. One of the most common genetic changes observed in human malignancies are mutations of the p53 protein. p53 controls the transition of cells from the stationary (G1) to the replicative (S) phase of the cell cycle and prevents this transition in the presence of DNA damage. In other words, one of the main consequences of disabling p53 mutations is the accumulation and propagation of DNA damage, i.e. genetic changes. Common types of genetic changes in neoplastic cells are, in addition to point mutations, amplifications and gross, structural alterations, such as translocations.

The amplification of DNA sequences may indicate specific functional requirement as illustrated in the DHFR experimental system. Therefore, the amplification of certain oncogenes in malignancies points toward a causative role of these genes in the process of malignant transformation and maintenance of the transformed phenotype. This hypothesis has gained support in recent studies. For example, the bcl-2 protein was found to be amplified in certain types of non-Hodgkin's lymphoma. This protein inhibits apoptosis and leads to the progressive accumulation of neoplastic cells. Members of the gene family of growth factor receptors have been found to be amplified in various types of cancers, suggesting that overexpression of these receptors may make neoplastic cells less susceptible to limiting amounts of available growth factor. Examples include the amplification of the androgen receptor in recurrent prostate cancer during androgen deprivation therapy and the amplification of the growth factor receptor homologue ERB2 in breast cancer. Lastly, genes involved in intracellular signaling and control of cell cycle progression can undergo amplification during malignant transformation. This is illustrated by the amplification of the bcl-1 and ras genes in various epithelial and lymphoid neoplasms.

These earlier studies illustrate the feasibility of identifying amplified DNA sequences in neoplasms, because this approach can identify genes important for malignant transformation. The case of ERB2 also demonstrates the feasibility from a therapeutic standpoint, since transforming proteins may represent novel and specific targets for tumor therapy.

Several different techniques can be used to demonstrate amplified genomic sequences. Classical cytogenetic analysis of chromosome spreads prepared from cancer cells is adequate to identify gross structural alterations, such as translocations, deletions and inversions. Amplified genomic regions can only be visualized, if they involve large regions with high copy numbers or are present as extrachromosomal material. While cytogenetics was the first technique to demonstrate the consistent association of specific chromosomal changes with particular neoplasms, it is inadequate for the identification and isolation of manageable DNA sequences. The more recently developed technique of comparative genomic hybridization (CGH) has illustrated the widespread phenomenon of genomic amplification in neoplasms. Tumor and normal DNA are hybridized simultaneously onto metaphases of normal cells and the entire genome can be screened by image analysis for DNA sequences (hat are present in the tumor at an increased frequency. (WO 93/18,186; Gray et al., *Radiation Res.* 137 275–289 [1994]). As a screening method, this type of analysis has revealed a large number of recurring amplicons (a stretch of amplified DNA) in a variety of human neoplasms. Although CGH is more sensitive than classical cytogenetic analysis in identifying amplified stretches of DNA, it does not allow a rapid identification and isolation of coding sequences within the amplicon by standard molecular genetic techniques.

The most sensitive methods to detect gene amplification are polymerase chain reaction (PCR)-based assays. These assays utilize very small amount of tumor DNA as starting material, are exquisitely sensitive, provide DNA that is amenable to further analysis, such as sequencing and are suitable for high-volume throughput analysis.

The above-mentioned assays are not mutually exclusive, but are frequently used in combination to identify amplifications in neoplasms. While cytogenetic analysis and CGH represent screening methods to survey the entire genome for amplified regions, PCR-based assays are most suitable for the final identification of coding sequences, i.e. genes in amplified regions.

According to the present invention, such genes have been identified by quantitative PCR (S. Gelmini et al., Clin. Chem. 43, 752 [1997]), by comparing DNA from a variety of primary tumors, including breast, lung, colon, prostate, brain, liver, kidney, pancreas, spleen, thymus, testis, ovary, uterus, etc. tumor, or tumor cell lines, with pooled DNA from healthy donors. Quantitative PCR was performed using a TaqMan™ PCR instrument (ABI). Gene-specific primers and fluorogenic probes were designed based upon the coding sequences of the DNAs.

Human lung carcinoma cell lines include A549 (SRCC768), Calu-1 (SRCC769), Calu-6 (SRCC770), H157 (SRCC771), H441 (SRCC772), H460 (SRCC773), SKMES-1 (SRCC774) and SW900 (SRCC775), all available from ATCC. Primary human lung tumor cells usually derive from adenocarcinomas, squamous cell carcinomas, large cell carcinomas, non-small cell carcinomas, small cell carcinomas, and broncho alveolar carcinomas, and include, for example, SRCC724 (squamous cell carcinoma abbreviated as "SqCCa"), SRCC725 (non-small cell carcinoma, abbreviated as "NSCCa"), SRCC726 (adenocarcinoma, abbreviated as "AdenoCa"), SRCC727 (adenocarcinoma), SRCC728 (squamous cell carcinoma), SRCC729 (adenocarcinoma), SRCC730 (adeno/squamous cell carcinoma), SRCC731 (adenocarcinoma), SRCC732 (squamous cell carcinoma), SRCC733 (adenocarcinoma), SRCC734 (adenocarcinoma), SRCC735 (broncho alveolar carcinoma, abbreviated as "BAC"), SRCC736 (squamous cell carcinoma), SRCC738 (squamous cell carcinoma), SRCC739 (squamous cell carcinoma), SRCC740 (squamous cell carcinoma), SRCC740 (lung cell carcinoma, abbreviated as "LCCa").

Colon cancer cell lines include, for example, ATCC cell lines SW480 (adenocarcinoma, SRCC776), SW620 (lymph node metastasis of colon adenocarcinoma, SRCC777), COLO320 (adenocarcinoma, SRCC778), HT29 (adenocarcinoma, SRCC779), HM7 (carcinoma, SRCC780), CaWiDr(adenocarcinoma, srcc781), HCT 116 (carcinoma, SRCC782), SKCO1 (adenocarcinoma, SRCC783), SW403 (adenocarcinoma, SRCC784), LS174T (carcinoma, SRCC785), and HM7 (a high mucin producing variant of ATCC colon adenocarcinoma cell line LS 174T, obtained from Dr. Robert Warren, UCSF). Primary colon tumors include colon adenoocarcinomas designated ColT2 (SRCC742), ColT3 (SRCC743), ColT8 (SRCC744), ColT10 (SRCC745), ColT12 (SRCC746), ColT14 (SRCC747), ColT15 (SRCC748), ColT17 (SRCC750), ColT1 (SRCC751), ColT4 (SRCC752), ColT5 (SRCC753), ColT6 (SRCC754), ColT7 (SRCC755), ColT9 (SRCC756), ColT11 (SRCC757),ColT18 (SRCC758), and DcR3, BACrev, BACfwd, T160, and T159.

Human breast carcinoma cell lines include, for example, HBL100 (SRCC759), MB435s (SRCC760), T47D (SRCC761), MB468(SRCC762), MB175 (SRCC763), MB361 (SRCC764), BT20 (SRCC765), MCF7 (SRCC766), SKBR3 (SRCC767).

3. Tissue Distribution

The results of the gene amplification assays herein can be verified by further studies, such as, by determining mRNA expression in various human tissues.

As noted before, gene amplification and/or gene expression in various tissues may be measured by conventional Southern blotting, Northern blotting to quantitate the transcription of mRNA (Thomas, Proc. Natl. Acad. Sci. USA, 77:5201–5205 (1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence CT-1 polypeptide or against a synthetic peptide based on the DNA sequences provided herein or against exogenous sequence fused to CT-1 DNA and encoding a specific antibody epitope. General techniques for generating antibodies, and special protocols for Northern blotting and in situ hybridization are provided hereinbelow.

4. Chromosome Mapping

If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival. Chromosome mapping includes both framework and epicenter mapping. For further details see e.g., Stewart et al., Genome Research 7, 422433 (1997).

5. Antibody Binding Studies

The results of the gene amplification study can be further verified by antibody binding studies, in which the ability of anti-CT-1 antibodies to inhibit the effect of the CT-1 polypeptides on tumor (cancer) cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, Monoclonal Antibodies: A Manual of Techniques, pp.147–158 (CRC Press, Inc., 1987).

Competitive binding assays rely on the ability of a labeled standard to compete with the test sample analyte for binding with a limited amount of antibody. The amount ol target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

6. Cell-Based Tumor Assays

Cell-based assays and animal models for tumors (e.g. cancers) can be used to verify the findings of the gene amplification assay, and further understand the relationship between the genes identified herein and the development and pathogenesis of neoplastic cell growth. The role of gene products identified herein in the development and pathology of tumor orcancercan betested by using primary tumor cells or cells lines that have been identified to amplify the genes herein. Such cells include, for example, the breast, colon and lung cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumorogenic cell growth by exerting cytostatic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from tumors in transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642–648 [1985]).

7. Animal Models

A variety of well known animal models can be used to further understand the role of the genes identified herein in the development and pathogenesis of tumors, and to test the efficacy of candidate therapeutic agents, including antibodies, and other antagonists of the native polypeptides, including small molecule antagonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngencic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sept. 18, 1997).

Probably the most often used animal species in oncological studies are immunodeficient mice and, in particular, nude mice. The observation that the nude mouse with hypo/aplasia could successfully act as a host for human tumor xenografts has lead to its widespread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g. *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B 104–1-1 cell line (stable NIH-3T3 cell line transfected with the neu protooncogene); ras-transfected NIH-3T3 cells; Caco-2 (ATCC HTB-37); a moderately well-differentiated grade II human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48, 689–696 [19831]). Tumor cells can be introduced into animals, such as nude mice, by a variety of procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected as subdermal implants. In this location, the inoculum is deposited between the lower part of the dermal connective tissue and the s.c. tissue. Boven and Winograd (1991), supra.

Animal models of breast cancer can be generated, for example, by implanting rat neuroblastoma cells (from which the feud oncogen was initially isolated), or izeu -transformed NIH-3T3 cells into nude mice, essentially as described by Drebin et al. *PNAS USA* 83, 9129–9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54, 4726–4728 (1994) and Too et al., *Cancer Research* 55, 681–684 (1995). This model is based on the so-called "METAMOUSE™" sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146, 720 [1977]), which provide a highly controllable model system for studying the anti-tumor activities of various agents (Palladino et al., *J. Immunol.* 138, 4023–4032 [1987]). Briefly, tumor cells are propagated in vitro in cell culture. Prior to injection into the animals, the cell lines are washed and suspended in buffer, at a cell density of about $10 \times 10^6$ to $10 \times 10^7$ cells/ml. The animals are then infected subcutaneously with 10 to 100 µl of the cell suspension, allowing one to three weeks for a tumor to appear.

In addition, the Lewis lung (3LL) carcinoma of mice, which is one of the most thoroughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., *Br. J. Cancer* 41, suppl. 4,309 [1980]), and evidence indicates that tumors can be started from injection of even a single cell and that a very high proportion of infected tumor cells survive. For further information about this tumor model see Zacharski, *Haemostasis* 16, 300–320 [1986]).

One way of evaluating the efficacy of a test compound in an animal model is implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, *Proc. 6th Int. Workshop on Immune-Deficient Animals,* Wu and Sheng eds., Basel, 1989, 301. It is noted, however that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into genn lines (e.g., Van der Putten et al., *Proc. Natl. Acad. Sci. USA* 82, 6148–615; [1985]); gene targeting in embryonic stem cells (Thompson et al., *Cell* 56, 313–321 [1989electroporation of embryos (Lo, *Mol. Cel. Biol.*3, 1803–1814 [1983]); sperm-mediated gene transfer (Lavitrano et al., *Cell* 57, 717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or, head-to-tail tandems. Selective introduction of a transgene into a particular cell type is also possible by following, for example, the technique of Lasko et al., *Proc. Natl. Acad. Sci. USA* 89, 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as ill situ hybridization, Northern blot analysis, PCR, or immunocytochemistry. The animals are further examined for signs of tumor or cancer development.

Alternatively, "knock out" animals can be constructed which have a defective or altered gene encoding a CT-1 polypeptide identified herein, as a result of homologous recombination between the endogenous gene encoding the polypeptide and altered genomic DNA encoding the same polypeptide introduced into an embryonic cell of the animal. For example, cDNA encoding a particular CT-1 polypeptide can be used to clone genomic DNA encoding that polypeptide in accordance with established techniques. A portion of the genomic DNA encoding a particular CT-1 polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, by their ability to defend against certain pathological conditions and by their development of pathological conditions due to absence of the CT-1 polypeptide.

The efficacy of antibodies specifically binding the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography. Cats diagnosed with sublingual oral squamous cell tumors are excluded from the study. The tongue can become paralyzed as a result of such tumor, and even if the treatment kills the tumor, the animals may not be able to feed themselves. Each cat is treated repeatedly, over a longer period of time. Photographs of the tumors will be taken daily during the treatment period, and at each subsequent recheck. After treatment, each cat undergoes another computed tomography scan. Computed tomography scans and thoracic radiograns are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinoma in dogs and cats is a preferred model as its appearance and behavior are very similar to those in humans. However, the use of this model is limited by the rare occurrence of this type of tumor in animals.

8. Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular CT-1 polypeptide encoded by a nucleic acid sequence described herein, its interaction with that polypeptide can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, Nature (London) 340, 245–246 (1989); Chien et al., Proc. Natl. Acad. Sci. USA 88, 9578–9582 (1991)]as disclosed by Chevray and Nathans [Proc. Natl. Acad. Sci. USA 89, 5789–5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a CT-1-encoding gene identified herein and other intra- or extracellular components can be tested as follows: usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

9. Compositions and Methods for the Treatment of Tumors

The compositions useful in the treatment of tumors associated with the amplification of the genes identified herein include, without limitation, antibodies, small organic and inorganic molecules, peptides, phosphopeptides, antisense and ribozyme molecules, triple helix molecules, etc. that inhibit the expression and/or activity of the target gene product.

For example, antisense RNA and RNA molecule act to-directly block the translation of mRNA by hybridizing to targeted mRNA and preventing protein translation. When antisense DNA is used, oligodeoxyribonucleotides derived from the translation initiation site, e.g. between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g. Rossi, *Current Biology*4, 469–471 (1994), and PCT publication No. WO 97/33551 (published Sept. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g. PCT publication No. WO 97/33551, supra.

These molecules can be identified by any or any combination of the screening assays discussed hereinabove and/or by any other screening techniques well known for those skilled in the art.

9.1 Antibodies

Some of the most promising drug candidates according to the present invention are antibodies and antibody fragments which may inhibit the production or the gene product of the amplified genes identified herein and/or reduce the activity of the gene products.

i. Polyclonal Antibodies

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the CT-1 polypeptide or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

ii. Monoclonal Antibodies

The anti-CT-1 antibodies may, alternatively, be monoclonal antibodies. Monoclonal antibodies may be prepared using hybridoma methods, such as those described by Kohler and Milstem, *Nature,* 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the CT-1 polypeptide, including fragments, or a fusion protein of such protein or a fragment thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice,* Academic Press, (1986) pp.59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection (ATCC), Manassas, Va. Human myeloma and mouse-human heteromyeloma cell lines also have been described for the production of human monoclonal antibodies [Kozbor, *J. Immunol.,* 133:3001 (1984); Brodeur et al., *Monoclonal Antibody Production Techniques and Applications,* Marcel Dekker, Inc., New York, (1987) pp. 51–63].

The culture medium in which the hybridoma cells are cultured can then be assayed for the presence of monoclonal antibodies directed against CT-1 . Preferably, the binding specificity of monoclonal antibodies produced by the hybridoma cells is determined by immunoprecipitation or by an in vitro binding assay, such as radioimmunoassay (RIA) or enzyrne-linked immunoabsorbent assay (ELISA). Such techniques and assays are known in the art. The binding affinity of the monoclonal antibody can, for example, be determined by the Scatchard analysis of Munson and Pollard, *Anal. Biochem.,* 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mamnal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or mycloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

iii. Human and Humanized Antibodies

The anti-CT-1 antibodies may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

iv. Bispecific Antibodies

Bispecific antibodies are monoclonal, preferably human or humanized, antibodies that have binding specificities for at least two different antigens. In the present case, one of the binding specificities is for a CT-1 polypeptide, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, *Nature*, 305:537–539 [1983]). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.*, 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

v. Heteroconjugate Antibodies

Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

vi. Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191–1195 (1992) and Shopes, B. *J. Immunol.* 148:2918–2922 (1992). Homodimeric antibodies with enhanced anti-tumor activity may also be prepared using heterobifunctional cross-linkers as described in Wolff et al. *Cancer Research* 53:2560–2565 (1993). Alternatively, an antibody can be engineered which has dual Fc regions and may thereby have enhanced complement lysis and ADCC capabilities. See Stevenson et al., *Anti-Cancer Drug Design* 3:219–230 (1989).

vii. Immunoconjugates

The invention also pertains to immunoconjugates comprising an antibody conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officials inhibitor, gelonin, mitogellin, restrictocin, phenomycin, enomycin and the tricothecenes. A variety of radionuclides are available for the production of radioconjugated antibodies. Examples include $^{212}$Bi, $^{131}$In, $^{90}$Y and $^{186}$Re.

Conjugates of the antibody and cytotoxic agent are made using a variety of bifunctional protein coupling agents such as N-succinimidyl-3-(2-pyridyldithiol) propionate (SPDP), iminothiolate (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine, bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

viii. Immunoliposomes

The antibodies disclosed herein may also be formulated as immunoliposomes. Liposomes containing the antibody are prepared by methods known in the art, such as described in Epstein et al., *Proc. Natl. Acad. Sci. USA,* 82:3688 (1985); Hwang et al., *Proc. Natl Acad. Sci. USA,* 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286–288 (1982) via a disulfide interchange reaction. A chemotherapeutic agent (such as Doxorubicin) is optionally contained within the liposome. See Gabizon et al., *J. National Cancer Inst.* 81(19)1484 (1989).

10. Pharmaceutical Compositions

Antibodies specifically binding the product of an amplified gene identified herein, as well as other molecules identified by the screening assays disclosed hereinbefore, can be administered for the treatment of tumors, including cancers, in the form of pharmaceutical compositions.

If the protein encoded by the amplified gene is intracellular and whole antibodies are used as inhibitors, internalizing antibodies are preferred. However, lipofections or liposomes can also be used to deliver the antibody, or an antibody fragment, into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g. Marasco et al., *Proc. Natl. Acad. Sci. USA* 90, 7889–7893 [1993]).

Therapeutic formulations of the antibody are prepared for storage by mixing the antibody having the desired degree of purity with optional pharmaceutically acceptable carriers, excipients or stabilizers (*Remington's Pharmaceutical Sciences* 16th edition, Osol, A. Ed. [1980]), in the form of lyophiaized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, ordextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEENT™, PLURONICS™ or polyethylene glycol (PEG).

Non-antibody compounds identified by the screening assays of the present invention can be formulated in an analogous manner, using standard techniques well known in the art.

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. Wheh encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

11. Methods of Treatment

It is contemplated that the antibodies and other anti-tumor compounds of the present invention may be used to treat varios conditions, including those characterized by overexpression and/or activation of the amplified genes identified herein. Exemplary conditions or disorders to be treated with such antibodies and other compounds, including, but not limited to, small organic and inorganic molecules, peptides, antisense molecules, etc. include benign or malignant tumors (e.g. renal, liver, kidney, bladder, breast, gastric, ovarian, colorectal, prostate, pancreatic, ling, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The anti tumor agents of the present invention, e.g. antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral topical, or inhalation routes. Intravenous administration of the antibody is preferred.

Other therapeutic regimens may be combined with the administration of the anti-cancer agents, e.g. antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers'instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent, e.g. antibody, or may be given simultaneously therewith. The antibody may be combined with an anti-oestrogen compound such as taimoxifen or an anti-progesterone such as onapristone (see, EP 616812) in dosages known for such molecules.

It may be desirable to also administer antibodies against other tumor associated antigens, such as antibodies which bind to theErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration for administration of the antibody of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent, e.g. an antibody herein will depend on the type of disease to be treated, as defined above, the severity and course of the disease, whether the agent is administered for preventive or therapeutic purposes, previous therapy, the patient's clinical history and response to the agent, and the discretion of the attending physician. The agent is suitably administered to the patient at one time or over a series of treatments.

For example, depending on the type and severity of the disease, about 1 μg/kg to 15 mg/kg (e.g. 0.1–20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

12. Articles of Manufacture

In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g. an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

13. Diagnosis and Prognosis of Tumors

While cell surface proteins, such as growth receptors overexpressed in certain tumors are excellent targets for drug candidates or tumor (e.g. cancer) treatment, the same proteins along with secreted proteins encoded by the genes amplified in tumor cells find additional use in the diagnosis and prognosis of tumors. For example, antibodies directed against the proteins products of genes amplified in tumor cells can be used as tumor diagnostics or prognostics.

For example, antibodies, including antibody fragments, can be used to qualitatively or quantitatively detect the expression of proteins encoded by the amplified genes ("marker gene products"). The antibody preferably is equipped with a detectable, e.g. fluorescent label, and binding can be monitored by light microscopy, flow cytometry, fluorimetry, or other techniques known in the art. These techniques are particularly suitable, if the amplified gene encodes a cell surface protein, e.g. a growth factor. Such binding assays are performed essentially as described in section 5 above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va. Unless otherwise noted, the present invention uses standard procedures of recombinant DNA technology, such as those described hereinabove and in t he following textbooks: Sambrook et al., *Molecular Cloning: A Laboratory Manual,* Cold Spring Harbor Press N.Y., 1989; Ausubel et al., *Current Protocols in Molecular Biology,* Green Publishing Associates and Wiley Interscience, N.Y., 1989; Innis et al., *PCR Protocols: A Guide to Methods and Applications,* Academic Press, inc., N.Y., 1990; Harlow et al., *Antibodies: A Laboratory Manual,* Cold Spring Harbor Press, Cold Spring Harbor, 1988; Gait, M. J., *Oligonucleotide Synthesis,* IRL Press, Oxford, 1984; R. I. Freshney, *Animal Cell Culture,* 1987; Coligan et al., *Current Protocols in Immunology,* 1991.

EXAMPLE 1

Gene Amplification

This example shows that the CT-1-encoding gene is amplified in the genome of certain human lung and colon cancer cell lines. Amplification is associated with overexpression of the gene product, indicating that the CT-1 proteins are useful targets for therapeutic intervention in certain cancers such as colon, lung, breast and other cancers. Therapeutic agent may take the form of antagonists of CT-1-encoding gene products, for example, murine-human chimeric, humanized or human antibodies against a CT-1 (CT-1) polypeptide.

The starting material for the screen was genomic DNA isolated from a variety of cancers. The DNA is quantitated precisely, e.g. fluorometrically. As a negative control, DNA was isolated from the cells of ten normal healthy individuals which was pooled and used as assay controls for the gene copy in healthy individuals (not shown). The 5' nuclease assay (for example, TaqMan™ nuclease assay from Applied Biosystems USA) and real-time quantitative PCR (for example, ABI Prizm 7700 Sequence Detection System™ (Perkin Elmer, Applied Biosystems Division, Foster City, Calif.)), were used to find genes potentially amplified in certain cancers. The results were used to determine whether the DNA encoding CT-1 is over-represented in any of the primary lung or colon cancers or cancer cell lines that were screened. The primary lung cancers were obtained from individuals with tumors of the type and stage as indicated in Table I. An explanation of the abbreviations used for the designation of the primary tumors listed in Table 1 and the primary tumors and cell lines referred to throughout this example has been given hereinbefore. The results of the Taqman™ PCR analyses are reported in delta (Δ) Ct units. One unit corresponds to one PCR cycle or approximately a 2-fold amplification relative to normal, two units corresponds to 4-fold, 3 units to 8-fold amplification and so on. Quantitation was obtained using primers and a Taqman™ Fluorescent probe derived from the CT-1-encoding gene. Regions of CT-1 which are most likely to contain unique nucleic acid sequences and which are least likely to have spliced out introns are preferred for the primer and probe derivation e.g. a 3'-untranslated region. The sequences for the primers and probes (forward, reverse and probe) used for the CT-1 gene amplification were as follows:
CT-1 (DNA58125):
58125.tm.f1
5'-TTCCCAGCCTCTCTTTGCTTT-3' (SEQ ID NO: 4)
58125.tm.r1

5'-TCAGACGGAGTTACCATGCAGA-3' (SEQ ID NO: 5)
58125.tm.p1
5'-TGCCCCGTTCTCTTAACTCTTGGACCC-3' (SEQ ID NO: 6)

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700™ Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample when comparing cancer DNA results to normal human DNA results.

Table 1 describes the stage, T stage and N stage, of various primary tumors which were used to screen the CT-1 compounds of the invention.

TABLE 1

Primary Lung and Colon Tumor Profiles

| Primary Tumor | Stage | Other Stage | Dukes Stage | T Stage | N Stage |
|---|---|---|---|---|---|
| Human lung tumor SqCCA (SRCC724) [LT1] | IB | — | — | T1 | N1 |
| Human lung tumor NSCCa (SRCC725) [LT1a] | IA | — | — | T3 | N0 |
| Human lung tumor AdenoCa (SRCC726) [LT2] | IB | — | — | T2 | N0 |
| Human lung tumor AdenoCa (SRCC727) [LT3] | IB | — | — | T1 | N2 |
| Human lung tumor SqCCq (SRCC728) [LT4] | IIB | — | — | T2 | N0 |
| Human lung tumor AdenoCa (SRCC729) [LT6] | IV | — | — | T1 | N0 |
| Human lung tumor Aden/SqCCa (SRCC730) [LT7] | IB | — | — | T1 | N0 |
| Human lung tumor AdenoCa (SRCC731) [LT9] | IIB | — | — | T2 | N0 |

TABLE 1-continued

Primary Lung and Colon Tumor Profiles

| Primary Tumor | Stage | Other Stage | Dukes Stage | T Stage | N Stage |
|---|---|---|---|---|---|
| Human lung tumor SqCCa (SRCC732) [LT10] | IA | — | — | T2 | N1 |
| Human lung tumor AdenoCa (SRCC733) [LT11] | IB | — | — | T1 | N1 |
| Human lung tumor AdenoCa (SRCC734) [LT12] | IIA | — | — | T2 | N0 |
| Human lung tumor BAC (SRCC735) [LT13] | IB | — | — | T2 | N0 |
| Human lung tumor SqCCa (SRCC736) [LT15] | IB | — | — | T2 | N0 |
| Human lung tumor SqCCa (SRCC737) [LT16] | IB | — | — | T2 | N0 |
| Human lung tumor SqCCa (SRCC738) [LT17] | IIB | — | — | T2 | N1 |
| Human lung tumor SqCCa (SRCC739) [LT18] | IB | — | — | T2 | N0 |
| Human lung tumor SqCCa (SRCC740) [LT19] | IB | — | — | T2 | N0 |
| Human lung tumor LCCa (SRCC741) [LT21] | IIB | — | — | T3 | N1 |
| Human colon AdenoCa (SRCC742) [ColT2] | — | M1 | D | pT4 | N0 |
| Human colon AdenoCa (SRCC743) [ColT3] | — | | B | pT3 | N0 |
| Human colon AdenoCa (SRCC744) [ColT8] | | | B | T3 | N0 |
| Human colon AdenoCa (SRCC745) [ColT10] | | | A | pT2 | N0 |
| Human colon AdenoCa (SRCC746) [ColT12] | | MO, R1 | B | T3 | N0 |
| Human colon AdenoCa (SRCC747) [ColT14] | | pMO, RO | B | pT3 | pN0 |
| Human colon AdenoCa (SRCC748) [ColT15] | | M1, R2 | D | T4 | N2 |
| Human colon AdenoCa (SRCC749) [ColT16] | | pMO | B | pT3 | pN0 |
| Human colon AdenoCa (SRCC750) [ColT17] | | | C1 | pT3 | pN1 |
| Human colon AdenoCa (SRCC751) [ColT1] | | MO, R1 | B | pT3 | N0 |
| Human colon AdenoCa (SRCC752) [ColT4] | | | B | pT3 | M0 |
| Human colon AdenoCa (SRCC753) [ColT5] | | G2 | C1 | pT3 | pN0 |
| Human colon AdenoCa (SRCC754) [ColT6] | | pMO, RO | B | pT3 | pN0 |
| Human colon AdenoCa (SRCC755) [ColT7] | | G1 | A | pT2 | pN0 |
| Human colon AdenoCa (SRCC756) [ColT9] | | G3 | D | pT4 | pN2 |
| Human colon AdenoCa (SRCC757) [ColT11] | | | B | T3 | N0 |
| Human colon AdenoCa (SRCC758) [ColT18] | | MO, RO | B | pT3 | pN0 |

DNA Preparation

DNA was prepared from cultured cell lines, primary tumors, normal human blood. The isolation was performed using purification kit, buffer set and protease and all from Quiagen, according to the manufacturer's instructions and the description below.

Cell culture Lysis

Cells were washed and trypsinized at a concentration of $7.5 \times 10^8$ per tip and pelleted by centrifuging at 1000 rpm for 5 minutes at 4° C., followed by washing again with ½ volume of PBS recentrifugation. The pellets were washed a third time, the suspended cells collected and washed 2× with PBS. The cells were then suspended into 10 mL PBS. Buffer C1 was equilibrated at 4° C. Quiagen protease #19155 was diluted into 6.25 ml cold ddH$_2$O to a final concentration of 20 mg/ml and equilibrated at 4° C. 10 mL of G2 Buffer was prepared by diluting Quiagen RNAse A stock (100 mg/ml) to a final concentration of 200 μg/ml.

Buffer C1 (10 mL, 4° C.) and ddH2O (40 mL, 4° C.) were then added to the 10 mL of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 mL Buffer C1 (at 4° C.) and 6 mL ddH$_2$O, followed by a second 4° C. centrifugation at 2500 rpm for 15 minutes. The nuclei were then resuspended into the residual buffer using 200 μl per tip. G2 buffer (10 ml) was added to the suspended nuclei while gentle vortexing was applied. Upon completion of buffer addition, vigorous vortexing was applied for 30 seconds. Quiagen protease (200 μl, prepared as indicated above) was added and incubated at 50° C. for 60 minutes. The incubation and centrifugation was repeated until the lysates were clear (e.g., incubating additional 30–60 minutes, pelleting at 3000×g for 10 min., 4° C.).

Solid human tumor sample preparation and lysis:

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNase A to a final concentration of 200 mg/ml (from 100 mg/ml stock). The tumor tissue was homogenated in 19 ml G2 buffer for 60 seconds using the large tip of the polytron in a laminar-flow TC hood to order to avoid inhalation of aerosols, and held at room temperature. Between samples, the polytron was cleaned by spinning at 2×30 seconds each in 2L ddH$_2$O, followed by G2 buffer (50 ml). If tissue was still present on the generator tip, the apparatus was disassembled and cleaned.

Quiagen protease (prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000×g for 10 min., 4° C.).

Human blood preparation and lysis:

Blood was drawn from healthy volunteers using standard infectious agent protocols and titrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNase A to a final concentration of 200 μg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddR$_2$O (4° C.). Vortexing was repeated until the pellet was white. The nuclei were then suspended into the residual buffer using a 200 μl tip. G2 buffer (10 ml) were added to the suspended nuclei while gently vortexing, followed by vigorous vortexing for 30 seconds. Quiagen protease was added (200 μl) and incubated at 50° C. for 60 minutes. The incubation and centrifugation was repeated until the lysates were clear (e.g., incubating additional 30–60 minutes, pelleting at 3000×g for 10 min., 4° C.).

Purification of cleared lysates:

(1) Isolation of genomic DNA

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C.). Isopropanol (10.5 ml) was added to each sample, the tubes covered with paraffin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatant discarded. The tubes were then placed on their side in a drying rack and dried 10 minutes at 37° C., taking care not to over dry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

Quantitaion of genomic DNA and preparation for gene amplification assay:

The DNA levels in each tube were quantified by standard $A_{260}$, $A_{280}$ spectrophotometry on a 1:20 dilution (5 μl DNA+95 μl ddH$_2$O) using the 0.1 ml quartz cuvetts in the Beckman DU640 spectrophotometer. $A_{260}/A_{280}$ ratios were in the range of 1.8–1.9. Each DNA sample was then diluted further to approximately 200 ng/ml in TE (pH 8.5). If the original material was highly concentrated (about 700 ng/μl), the material was placed at 50° C. for several hours until resuspended.

Fluorometric DNA quantitation was then performed on the diluted material (20–600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 μl, prepared within 12 hours of use) was diluted into 100 ml 1× TNE buffer. A 2 ml cuvette was filled with the fluorometer solution, placed into the machine, and the machine was zeroed. pGEM 3Zf(+) (2 μl, lot #360851026) was added to 2 ml of fluorometer solution and calibrated at 200 units. An additional 2 μl of pGEM 3Zf(+) DNA was then tested and the reading confirmed at 400±10 units. Each sample was then read at least in triplicate. When 3 samples were found to be within 10% of each other, their average was taken and this value was used as the quantification value.

The fluorometricly determined concentration was then used to dilute each sample to 10 ng/μl in ddH$_2$O. This was done simultaneously on all template samples for a single TaqMan™ plate assay (Applied Biosystems, INC.), and with enough material to run 500–1000 assays. The samples were tested in triplicate with Taqman™ primers and probe (Applied Biosystems, Inc.) both B-actin and GAPDH on a single plate with normal human DNA and no-template controls. The diluted samples were used provided that the Ct value of normal human DNA subtracted from test DNA was ±1 Ct. The diluted lot qualified genomic DNA was stored in 1.0 ml aliquots at −80° C. Aliquots which were subsequently to be used in the gene amplification assay were stored at 4° C. Each 1 ml aliquot is enough for 8–9 plates or 64 tests.

Gene amplification assay:

The CT-1 (cardiotrophin-1) compounds of the invention were screened in the following primary tumors and the resulting ΔCt values are reported in Table 2.

TABLE 2

Screening of DNA58125 ΔCt values in lung and colon primary tumor models

| Lung Tumor Panel 1 | ΔCt | Lung Tumor Panel 2 | ΔCt | Colon Tumor Panel 1 | ΔCt | Colon Tumor Panel 2 | ΔCt |
|---|---|---|---|---|---|---|---|
| LT1.1 | −0.07 | LT11 | 0.91 | ColT2 | 2.19 | ColT1 | 1.17 |
| LT1a | 0.79 | LT12 | 1.05 | ColT3 | 1.65 | ColT4 | 1.10 |
| LT2 | 0.25 | LT13 | 1.36 | ColT8 | 1.11 | ColT5 | 2.03 |
| LT3 | 0.92 | LT15 | 2.20 | ColT10 | 1.65 | ColT6 | 0.92 |
| LT4 | 0.56 | LT16 | 0.75 | ColT12 | 1.06 | ColT7 | 0.28 |
| LT6 | 0.45 | LT17 | 1.31 | ColT14 | 1.63 | ColT9 | 0.72 |
| LT7 | 0.61 | LT18 | 1.12 | ColT15 | 1.26 | ColT11 | 2.13 |
| LT9 | 0.59 | LT22 | 0.29 | ColT16 | 1.30 | ColT18 | 0.77 |
| LT10 | 0.81 | — | — | ColT17 | 0.89 | — | — |
| S.D. | 0.02 | — | 0.13 | — | 0.13 | — | 0.17 |

CT-1

CT-1 (cardiotrophin-1,DNA58125) was reexamined with both framework and epicenter mapping using tumors selected from the above initial screen. FIGS. 3–8 and Tables 3–5 provide the results of chromosome 16 mapping of the framework markers in lung and colon tumors. The framework markers are located approximately every 20 megabases and were used as controls for determining amplification. Tables 6–8 and FIGS. 9–12 show the results of chromosome 16 mapping of the epicenter markers near DNA58125.

TABLE 3

Framework Markers

| Map Position | Stanford Human Genome Center Marker Name |
|---|---|
| P7 | SHGC-2835 |
| P55 | SHGC-9643 |
| P99 | GATA7B02 |
| P154 | SHGC-33727 |
| P208 | SHGC-13574 |

The ΔCt values of the above described framework markers along Chromosome 16 relative to CT-1 are indicated for selected lung and colon tumors in Tables 4 and 5, respectively.

TABLE 4

Amplification of framework markers relative to DNA58125 in Lung Tumor

| Lung Tumor | Framework Markers (ΔCt) | | | | | |
|---|---|---|---|---|---|---|
| | P7 | P55 | P99 | P154 | P208 | DNA58125 |
| Panel 1 | | | | | | |
| LT1.1 | −3.62 | −0.07 | 0.03 | −0.22 | −0.06 | 0.18 |
| LT1a | −1.90 | −0.13 | 0.10 | 0.45 | 0.28 | 0.75 |
| LT2 | −0.41 | −0.05 | 0.07 | −0.07 | 0.41 | 0.36 |
| LT3 | 0.18 | −0.37 | −0.17 | −0.18 | 0.19 | 1.02 |
| LT4 | −3.58 | −0.25 | −0.13 | −0.05 | 0.04 | 0.65 |
| LT6 | −0.57 | −0.26 | 0.05 | −0.23 | 0.09 | 0.34 |
| LT7 | −1.60 | 0.46 | 1.14 | 0.25 | −0.54 | 0.43 |
| LT9 | −0.77 | −0.14 | 0.33 | −0.18 | 0.43 | 0.36 |

TABLE 4-continued

Amplification of framework markers relative to DNA58125 in Lung Tumor

| Lung Tumor | Framework Markers (ΔCt) | | | | | |
|---|---|---|---|---|---|---|
| | P7 | P55 | P99 | P154 | P208 | DNA58125 |
| LT10 | −2.60 | −0.28 | 0.20 | −0.02 | 0.39 | 0.50 |
| S.D. | 0.36 | 0.11 | 0.01 | 0.04 | 0.21 | 0.01 |
| Panel 2 | | | | | | |
| LT11 | −0.64 | −0.15 | −0.02 | −0.08 | −0.55 | 0.86 |
| LT12 | −1.19 | −0.11 | −0.50 | −0.74 | −0.97 | 1.00 |
| LT13 | −0.31 | −0.27 | 0.02 | −0.38 | −0.40 | 1.33 |
| LT15 | −0.90 | −1.90 | −0.07 | −0.18 | −0.39 | 1.83 |
| LT16 | −1.29 | −0.92 | −0.68 | −0.43 | −0.90 | 0.97 |
| LT17 | −0.13 | −0.15 | 0.02 | −0.15 | −0.52 | 1.03 |
| LT18 | −1.24 | −0.43 | −0.04 | −0.13 | −0.45 | 1.08 |
| LT22 | −1.86 | −0.29 | −0.09 | −0.12 | −0.26 | 0.05 |
| — | — | — | — | — | — | — |
| S.D. | 0.30 | 0.04 | 0.09 | 0.07 | 0.28 | 0.10 |

Figure 3:
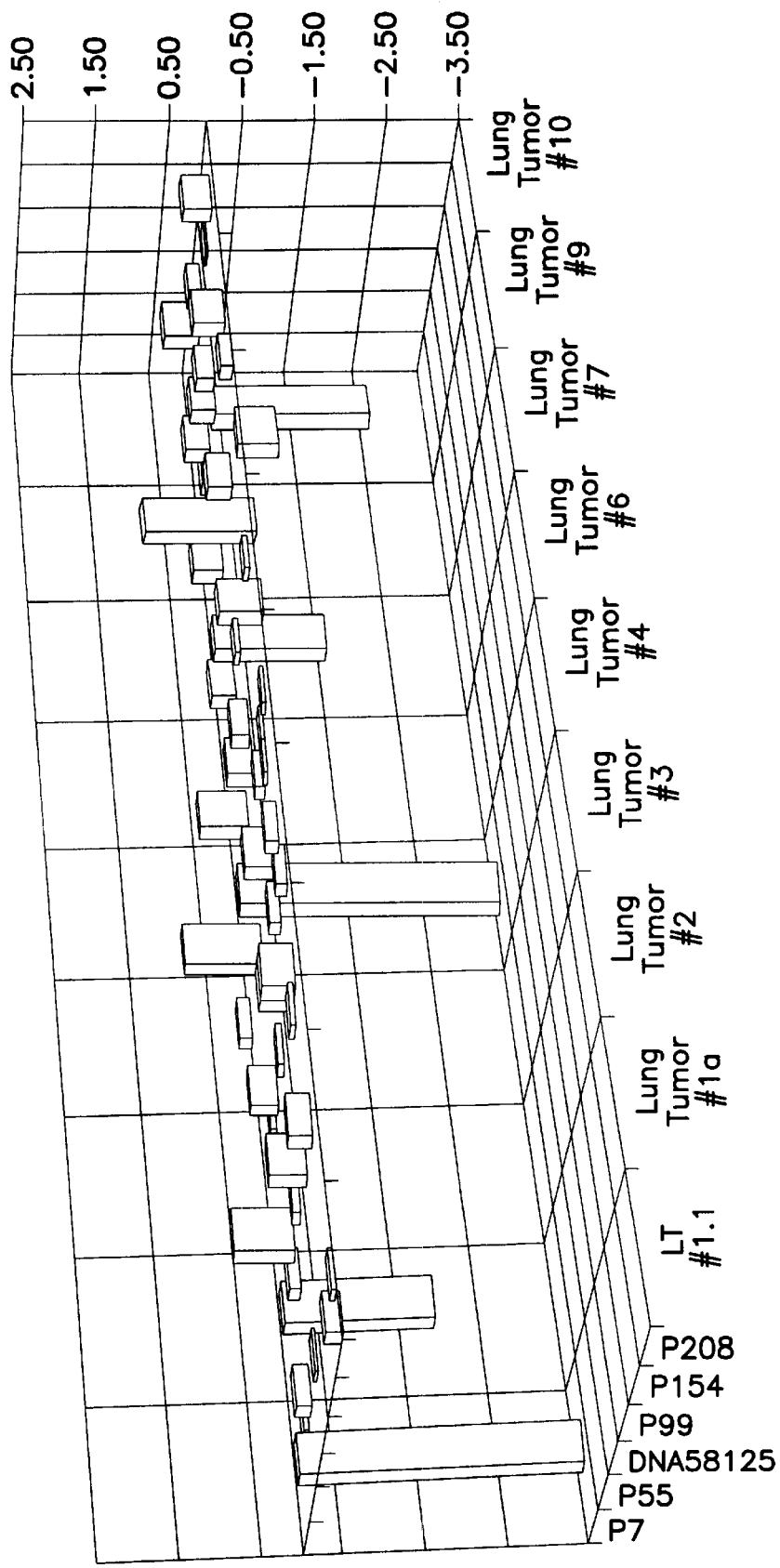
FIG. 3 is a three-dimensional representation of the results of a framework analysis of DNA58125 (cardiotrohin-1) on lung tumor Panel 1. The primary lung tumors tested are shown along the x-axis; the marker probes and DNA5812 are shown along the z-axis; and the relative genetic amplification in the area of each of the marker probes is shown as bars on the y-axis. Bars project above the zero plane for geneitc regions amplified relative to DNA58125 in healthy tissue, or below the zero plane indicating reduced genetic quantitation in that region.
Figure 4:
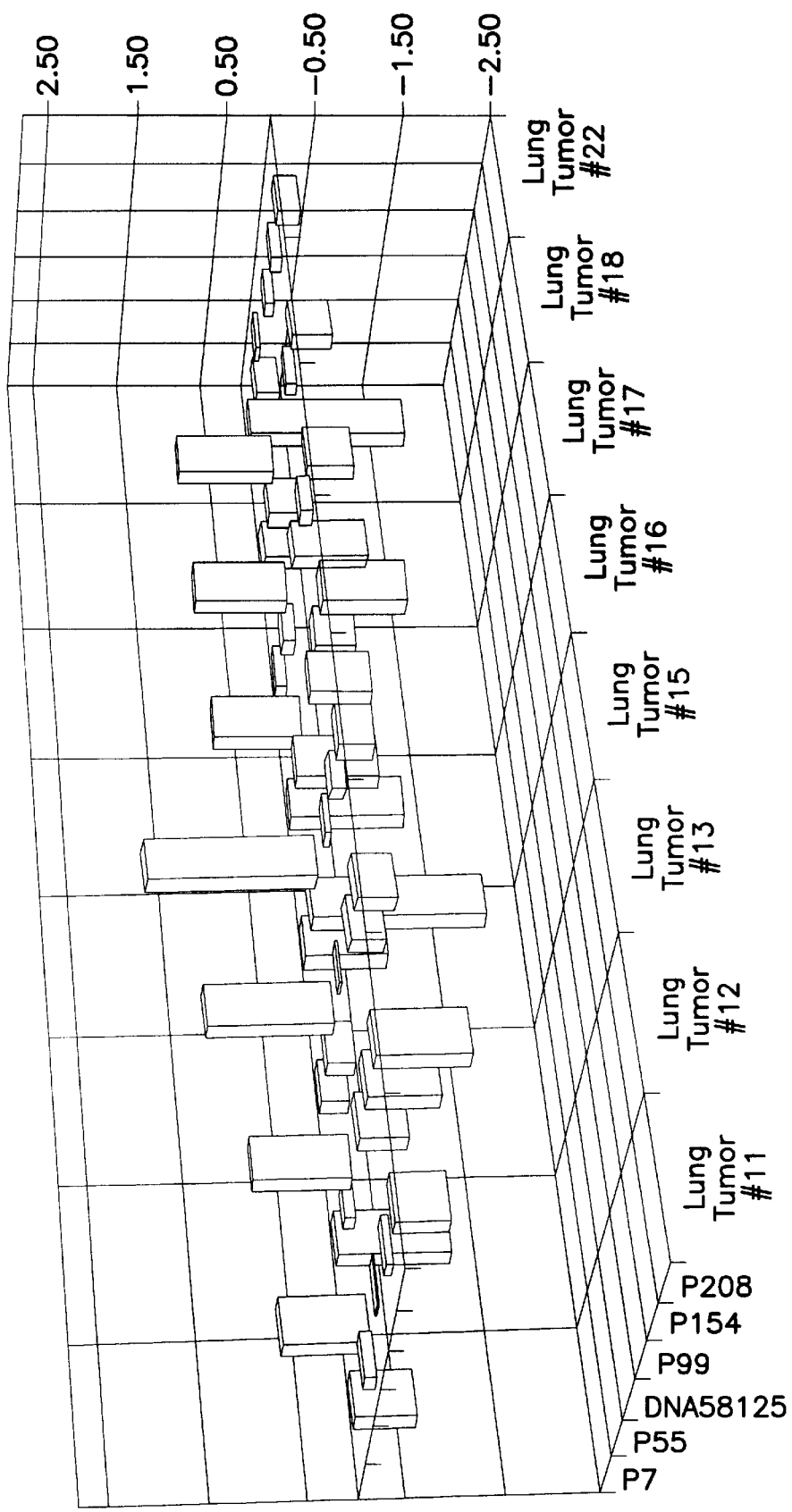
FIG. 4 is a three-dimensional representation of the results of a framework analysis of DNA58125 (cardiotrophin-1) on lung tumor Panel 2. The bar graph is arranged as generally described in FIG. 3.
Figure 5:
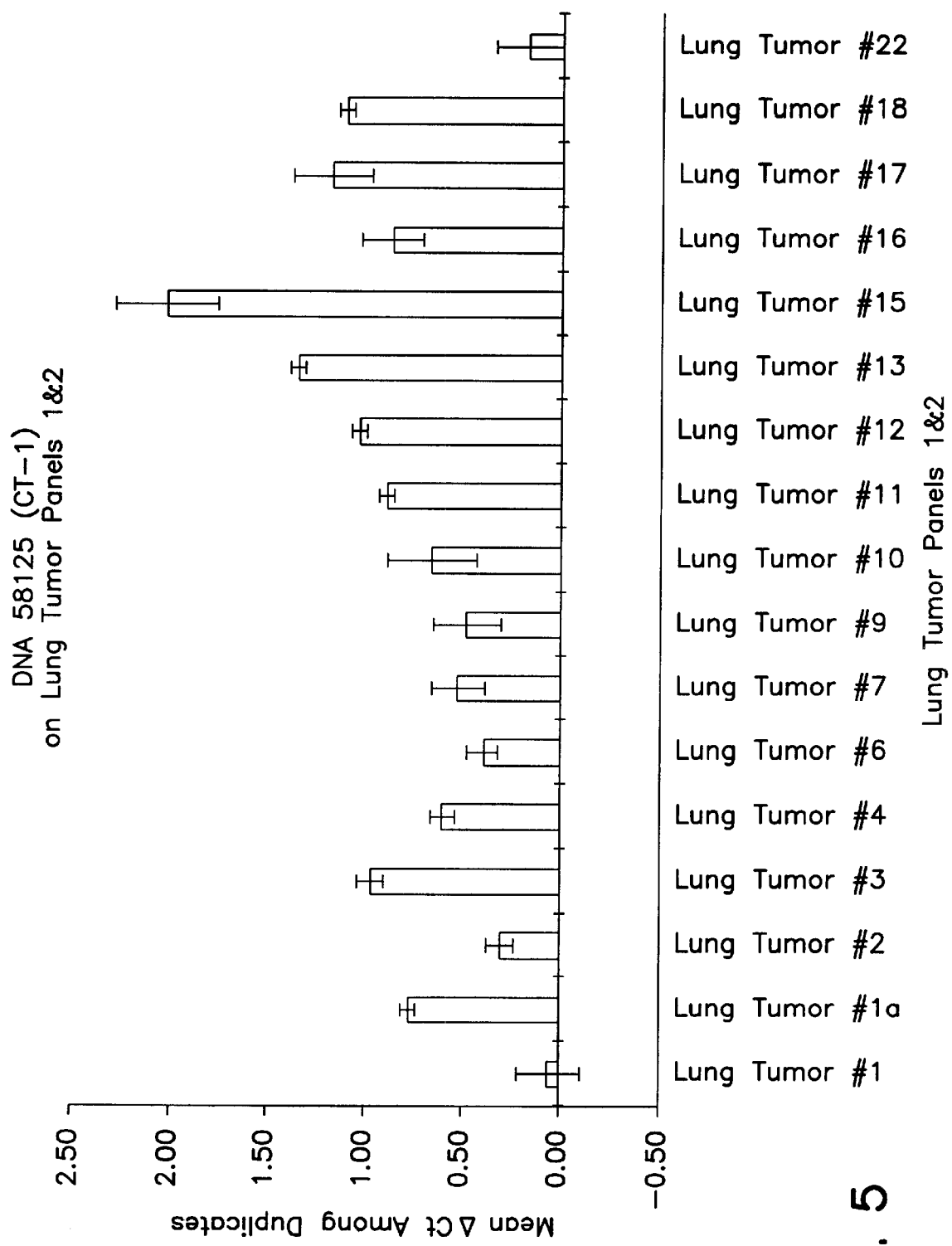
FIG. 5 is a two-dimensional bar graph summary of the results for DNA58125 from FIGS. 3 and 4. The mean ΔCt values determined for each of the lung tumors lines tested are shown.

FIGS. 3 and 4 provide a three-dimensional graphical representation of the data in Table 4, Panels 1 and 2 respectively. The lung tumors are plotted along the x-axis, the markers and DNA58125 are plotted along the z-axis, and the relative amplification of chromosome 16 in the region of the marker is indicated along the y-axis by the height of the bar. FIG. 5 is a two-dimensional bar graph summarizing the data in Table 4 for DNA58125 and showing that the chromosomal DNA encoding CT-1 is amplified in some of the lung tumors (mean ΔCt values above 1.0 are single underlined and values above 2.0 are double underlined).

TABLE 5

Amplification of framework markers relative to DNA58125 in Colon Tumor

| Colon Tumor | Framework Markers (ΔCt) | | | | | |
|---|---|---|---|---|---|---|
| | P7 | P55 | P99 | P154 | P208 | DNA58125 |
| Panel 1 | | | | | | |
| ColT2 | 2.72 | 0.93 | 0.72 | 0.48 | −0.13 | 2.27 |
| ColT3 | 0.01 | 0.07 | 0.53 | −0.27 | −0.52 | 1.34 |
| ColT8 | −1.01 | 1.05 | 0.69 | 0.60 | 0.04 | 1.23 |
| ColT10 | 0.95 | 0.84 | 0.75 | −0.17 | −0.57 | 1.74 |
| ColT12 | −0.73 | 0.49 | 0.71 | 0.60 | −0.88 | 1.13 |
| ColT14 | −0.16 | 1.49 | 0.83 | 0.33 | −0.38 | 1.74 |
| ColT15 | −1.23 | 0.72 | 0.60 | −0.29 | −0.70 | 1.30 |
| ColT16 | 0.05 | 1.07 | 0.59 | −0.13 | −0.66 | 0.93 |
| ColT17 | 0.27 | 1.06 | 0.83 | −0.15 | −0.77 | 0.91 |
| S.D. | 0.15 | 0.67 | 0.88 | 0.57 | 0.49 | 0.04 |
| Panel 2 | | | | | | |
| ColT1 | −0.73 | 0.35 | −0.09 | 0.05 | −0.03 | 1.08 |
| ColT4 | −0.99 | −0.07 | −0.61 | −0.43 | −0.09 | 1.13 |
| ColT5 | 0.09 | 0.34 | −0.04 | −0.19 | −0.01 | 2.17 |
| ColT6 | −1.36 | −0.29 | −0.03 | −0.16 | 0.27 | 1.41 |
| ColT7 | −1.36 | 0.09 | −0.18 | −0.17 | −0.13 | 0.24 |
| ColT9 | 1.73 | 0.29 | 0.08 | 0.22 | 0.13 | 0.95 |
| ColT11 | 1.03 | 0.51 | −0.08 | 0.61 | 0.16 | 2.24 |
| ColT18 | 0.32 | 0.81 | 0.74 | 0.55 | 0.36 | 1.04 |
| S.D. | 0.23 | 0.03 | 0.27 | 0.23 | 0.26 | 0.04 |

Figure 6:
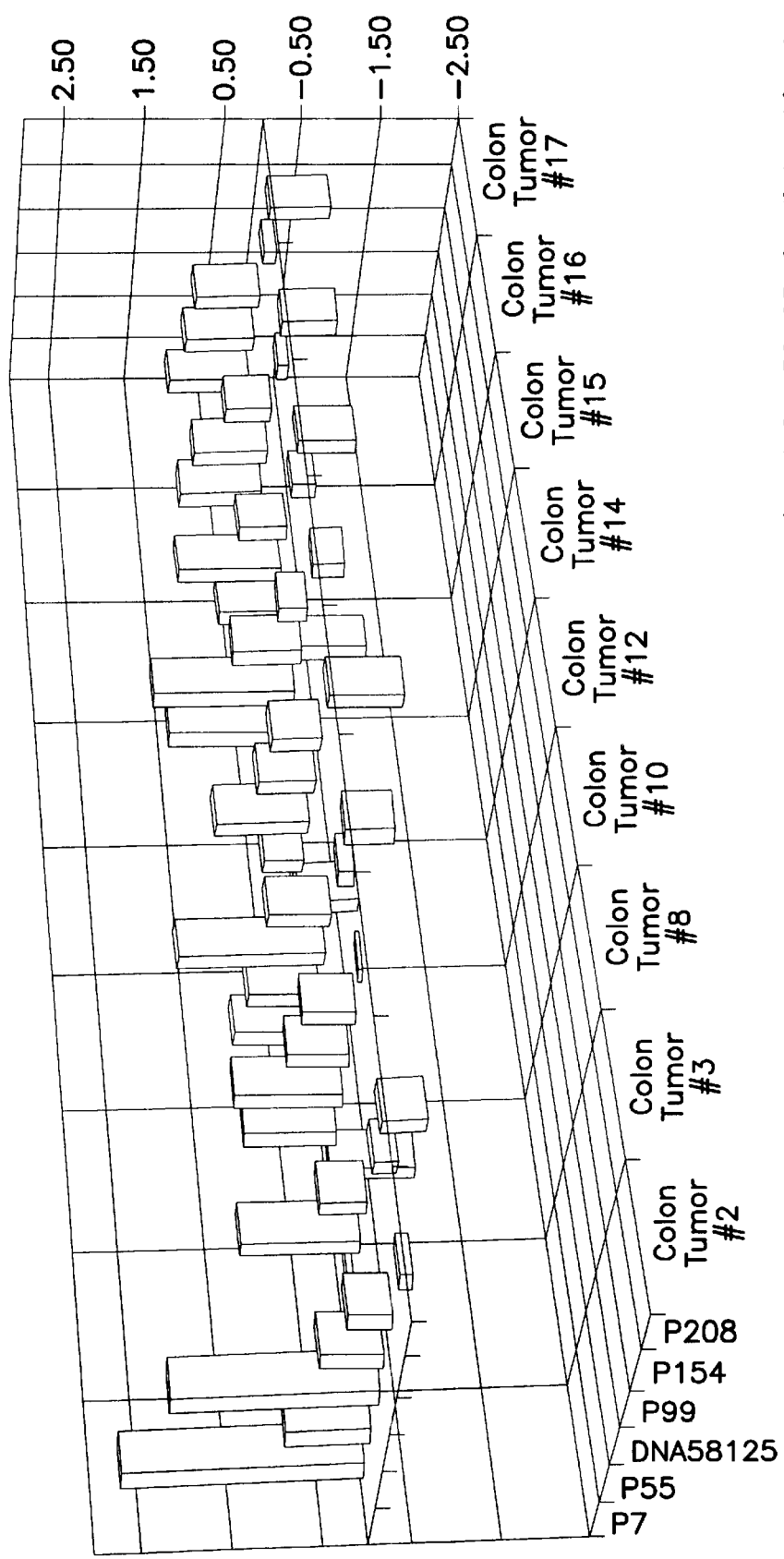
FIG. 6 is a three-dimensional representation of the results of a framework analysis of DNA58125 (cardiotrophin-1) on colon tumor Panel 1. The primary colon tumors tested are shown along the x-axis; the marker probes and DNA58125 are shown along the z-axis; and the relative genetic amplification in the area of each of the marker probes is shown as bars on the y-axis. Bars project above the zero plane for genetic regions amplified relative to DNA58125 in healthy tissue, or below the zero plane indicating reduced genetic quantitation in that region.
Figure 7:
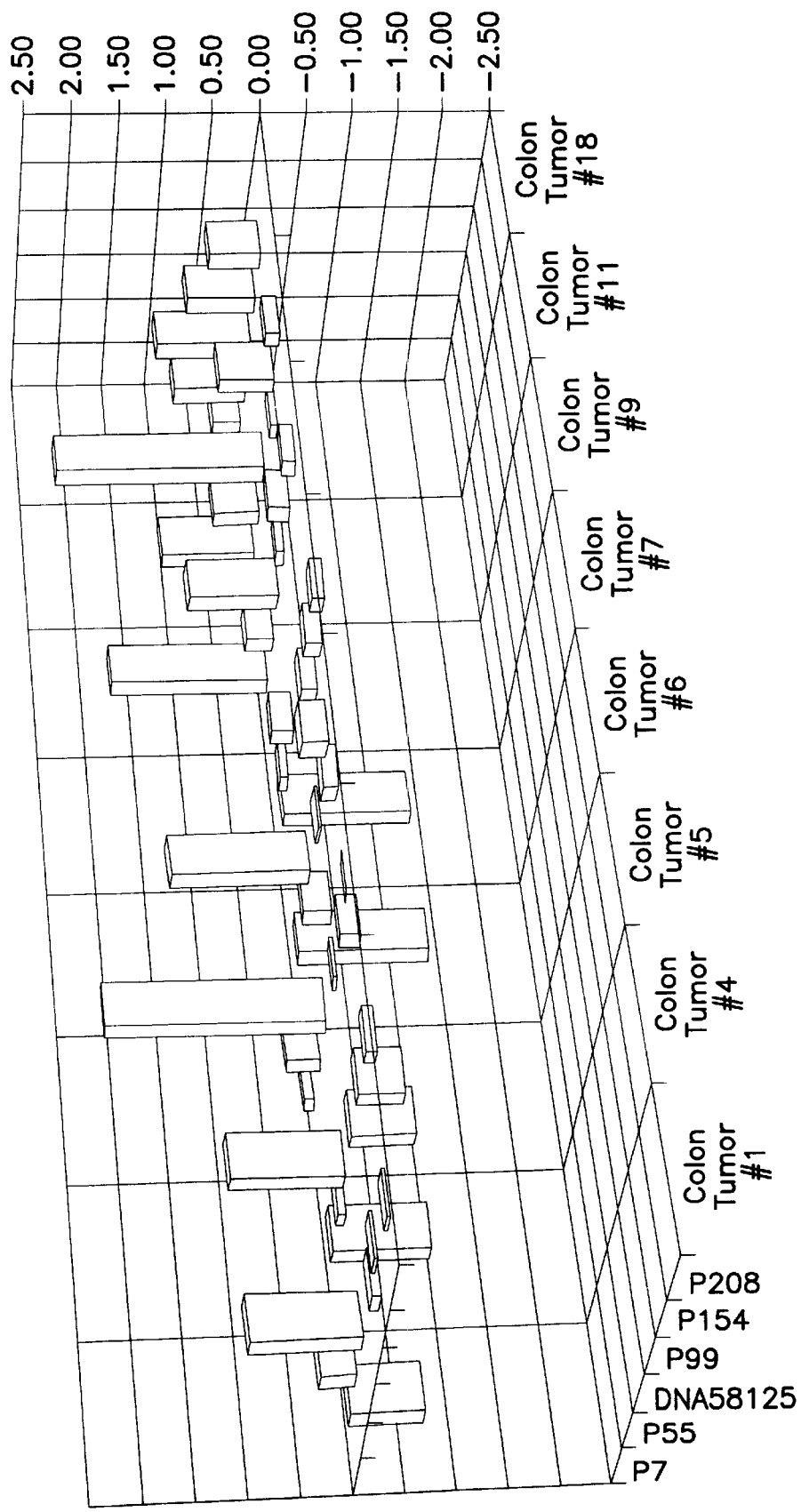
FIG. 7 is a three-dimensional representation of the results of a framework analysis of DNA58125 (cardiotrophin-1) on colon tumor Panel 2. The bar graph is arranged as generally described in FIG. 6.
Figure 8:
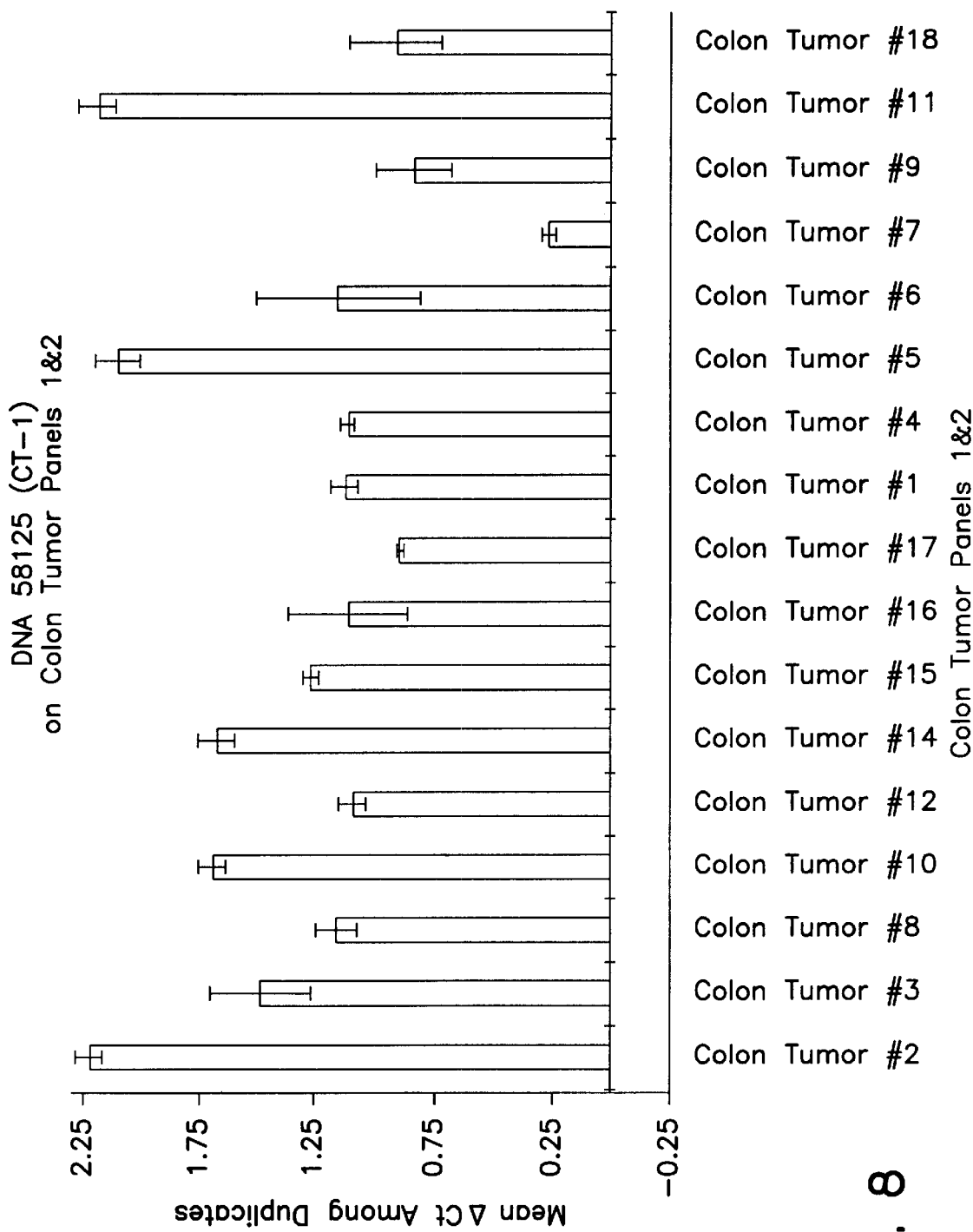
FIG. 8 is a two-dimensional bar graph summary of the results for DNA58125 from FIGS. 6 and 7. The mean ΔCt values determined for each of the colon tumors tested are shown.
Figure 9:
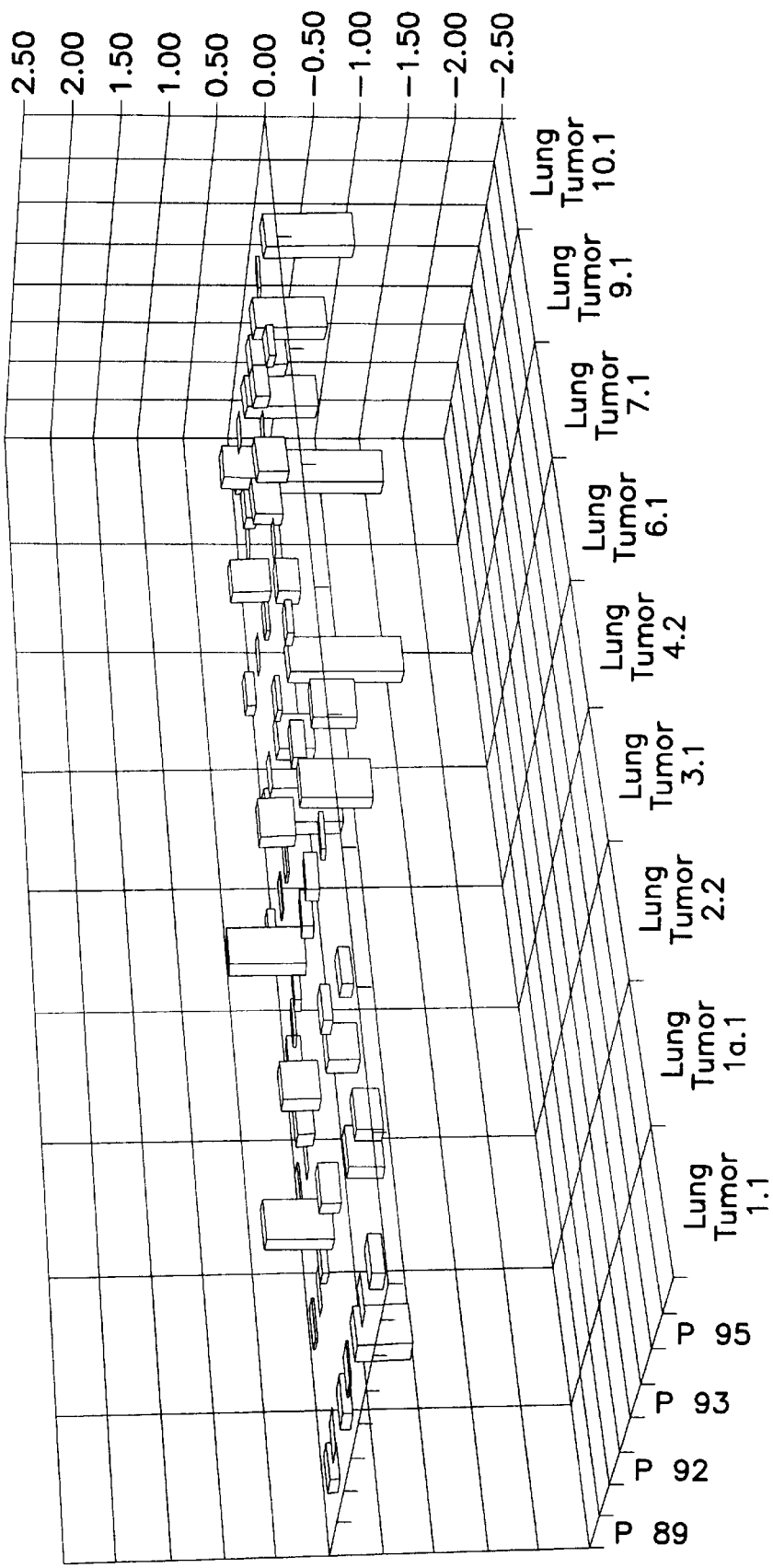
FIG. 9 is a three-dimensional representation of the results of an epicenter analysis of DNA58125 (cardiotrophin-1) on lung tumor Panel 1. The bar graph is arranged as generally described in FIG. 3.
Figure 10:
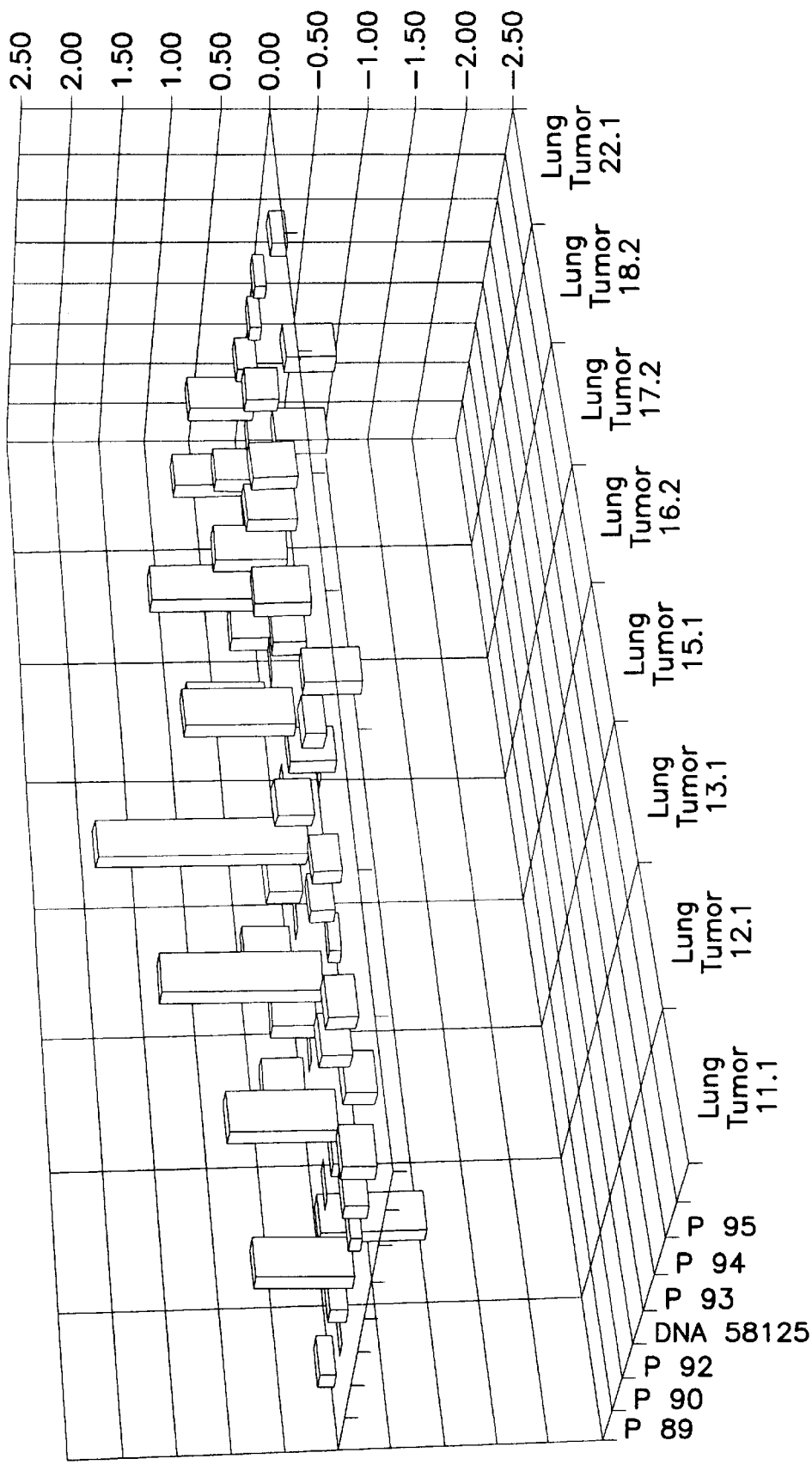
FIG. 10 is a three dimensional representation of the results of an epicenter analysis of DNA58125 (CT-1 ) on lung tumor Panel 2. The bar graph is arranged as generally described in FIG. 3.
Figure 11:
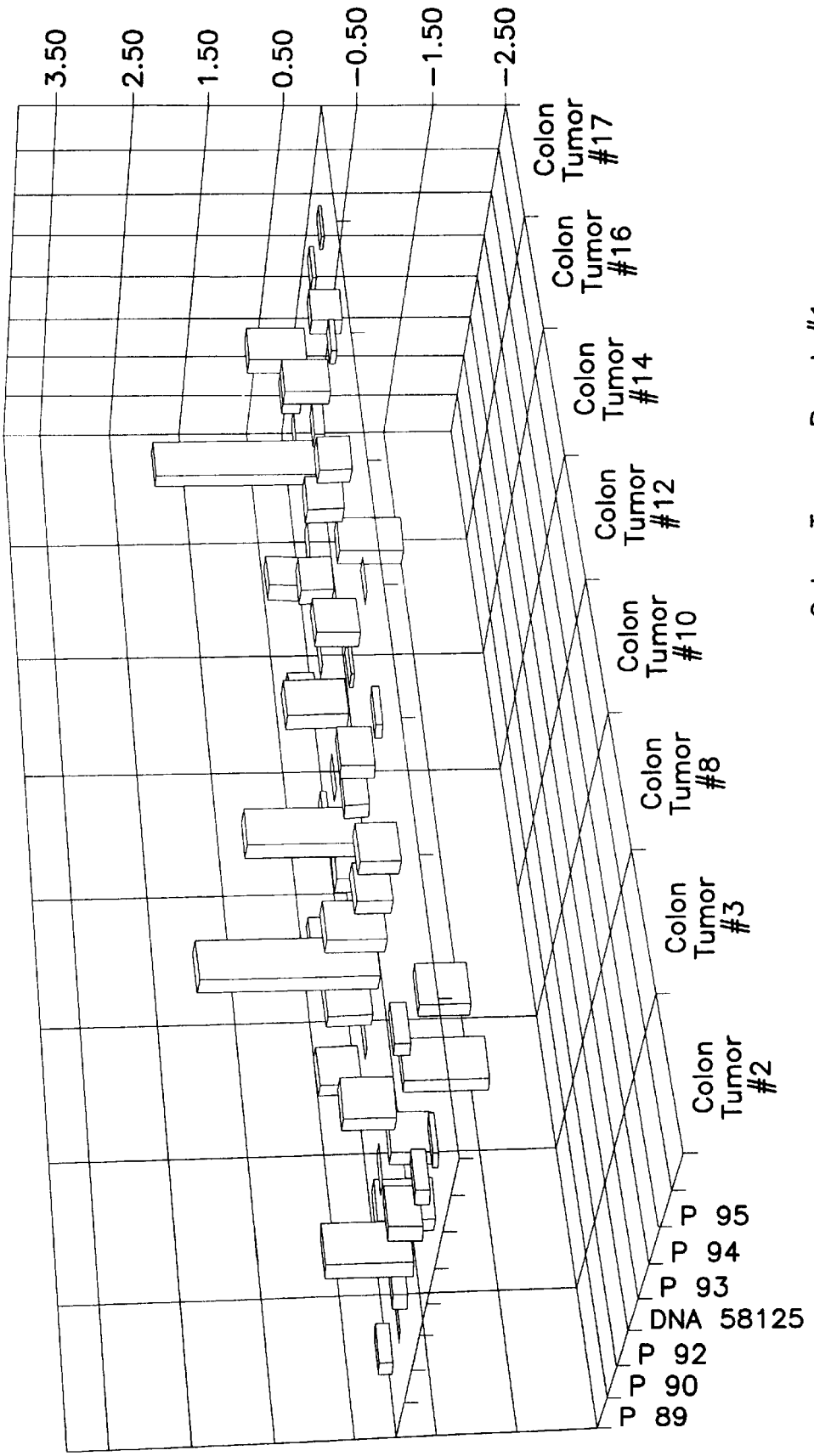
FIG. 11 is a three dimensional representation of the results of an epicenter analysis of DNA58125 (CT-1 ) on colon tumor Panel 1. The bar graph is arranged as generally described in FIG. 6.
Figure 12:
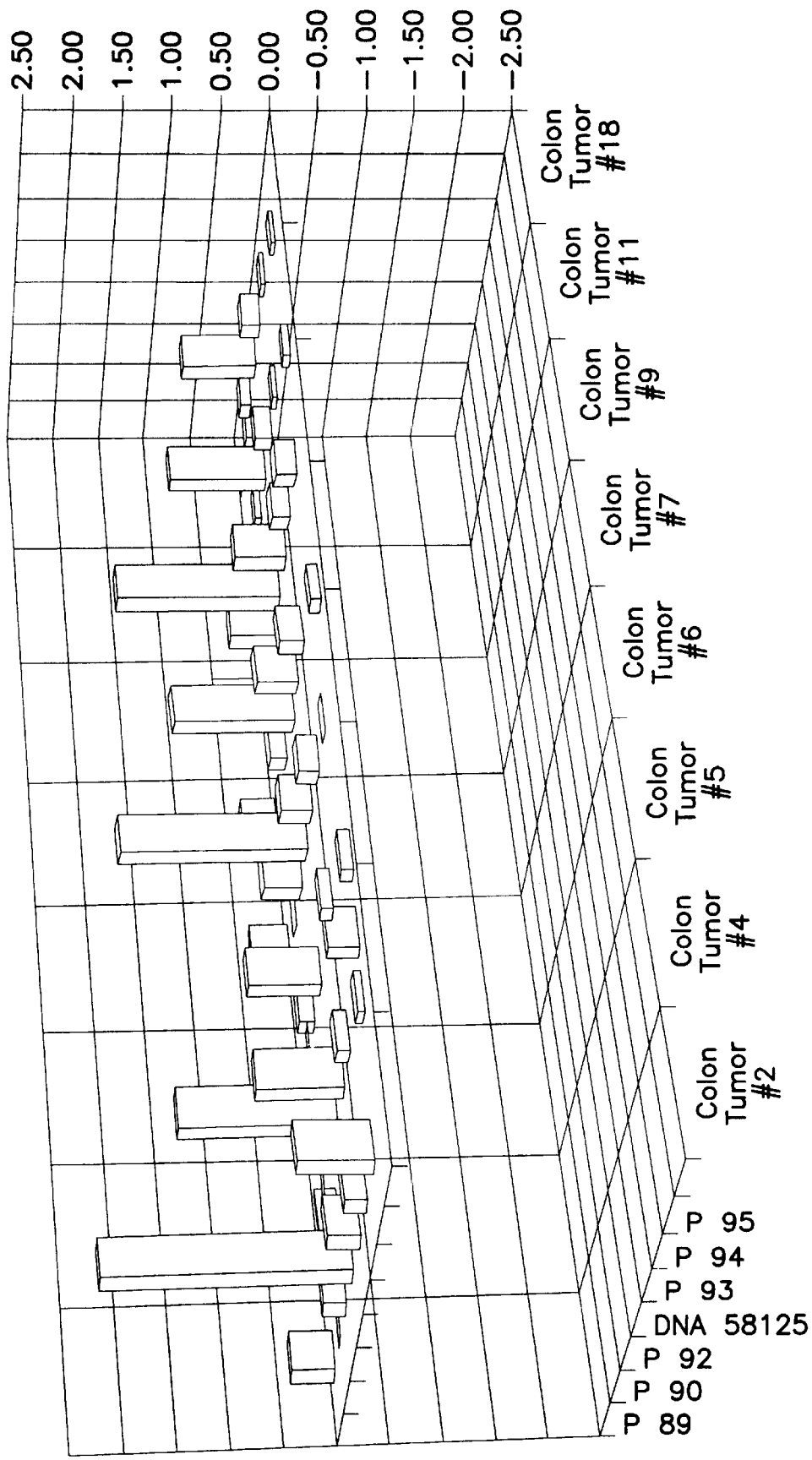
FIG. 12 is a three dimensional representation of the results of an epicenter analysis of DNA58125 (CT-1 ) on colon tumor Panel 2. The bar graph is arranged as generally described in FIG. 6.

FIGS. 6 and 7 provide a three-dimensional graphical representation of the data in Table 5, Panels 1 and 2 respectively. The colon tumors are plotted along the x-axis, the markers and DNA58125 are plotted along the z-axis, and the relative amplification of chromosome 16 in the region of the marker is indicated along the y-axis by the height of the bar. FIG. 8 is a two-dimensional bar graph summarizing the data in Table 5 for DNA58125 and showing that the chromosomal DNA encoding CT-1 is amplified in several of the colon tumors (mean ΔCt values above 1.0 are single underlined and values above 2.0 are double underlined).

Table 6 describes the epicenter markers that were employed in association with CT-1 (DNA58125). These markers are located in close proximity to DNA58125 and are used to assess the amplification status of the region of chromosome 16 in which DNA58125 is located. The distance between individual markers is measured in centirays, which is a radiation breakage unit approximately equal to a 1% chance of a breakage between two markers. One cR is very roughly equivalent to 20 kilobases. The marker SHGC-36123 is the marker found to be the closest to the location on chromosome 16 where DNA58125 most closely maps. However, the Taqman™ primers and probes (Applied Biosystem, Inc.) for SHGC-2726 failed in our assay due to technical difficulties related to PCR.

TABLE 6

Epicenter Markers

| Map Position on Chromosome 16 | Stanford Human Genome Center Marker Name | Distance to Next Marker (cR[1]) |
|---|---|---|
| P89 | SHGC-11302 | 27 |
| P90 | EST00087 | 8 |
| P92 | SHGC-2726 | 23 |
| DNA58125 | — | — |
| P93 | SHGC-36123[2] | 42 |
| P94 | SHGC-35326 | 23 |
| P95 | IB391 | — |

[1]cR = Centiray. Distance between markers is measured in cR, which is a radiation breakage unit approximately equal to a one percent chance of a breakage between two markers.
One cR corresponds roughly to 20 kilobases.
SHGC-36123 is the marker to which DNA58125 most closely maps.

Table 7 indicates the ΔCt values for results of epicenter mapping relative to DNA58125 in lung tumors, indicating the relative amplification in the region more immediate to the actual location of DNA58125 along chromosome 16.

TABLE 7

Amplification of Epicenter Markers Relative to DNA58125 in Lung Tumors

| | P89 | P90 | P92 | P93 | P94 | P95 | DNA58125 |
|---|---|---|---|---|---|---|---|
| Panel 1 | | | | | | | |
| LT1.1 | −0.11 | 0.00 | −0.10 | −0.52 | −0.01 | −0.13 | −0.02 |
| LT1a.1 | −0.03 | 0.00 | 0.06 | 0.19 | −0.33 | −0.25 | 0.65 |
| LT2.2 | 0.02 | 0.00 | 0.17 | −0.32 | 0.11 | −0.13 | 0.38 |
| LT3.1 | −0.15 | 0.00 | 0.05 | 0.10 | 0.13 | 0.04 | 0.77 |
| LT4.2 | 0.08 | 0.00 | 0.02 | −0.72 | 0.15 | −0.43 | 0.36 |
| LT6.1 | −0.82 | 0.00 | −0.40 | −1.18 | 0.09 | 0.23 | 0.07 |
| LT7.1 | 0.09 | 0.00 | −0.04 | 0.03 | 0.29 | 0.32 | 0.41 |
| LT9.1 | −0.09 | 0.00 | 0.12 | 0.04 | 0.18 | 0.09 | 0.40 |
| LT10.1 | −1.65 | 0.00 | −0.79 | 0.78 | 0.00 | −0.93 | −0.43 |
| S.D. | 0.29 | Failed | 0.25 | 0.88 | 0.04 | 0.18 | 0.11 |
| Panel 2 | | | | | | | |
| LT11.1 | 0.15 | 0.00 | 0.17 | 0.10 | 0.23 | 0.31 | 0.91 |
| LT12.1 | −1.03 | 0.00 | −0.07 | −0.30 | 0.29 | 0.27 | 1.02 |
| LT13.1 | 0.42 | 0.00 | 0.44 | −0.12 | 0.23 | 0.27 | 1.52 |
| LT15.1 | 0.48 | 0.00 | 0.35 | 0.37 | 0.00 | 0.22 | 2.04 |
| LT16.2 | −0.09 | 0.00 | −0.47 | −0.62 | 0.32 | 0.54 | 1.09 |
| LT17.2 | 0.81 | 0.00 | 0.46 | 0.72 | 0.46 | 0.45 | 1.32 |
| LT18.2 | −0.10 | 0.00 | −0.35 | −0.56 | 0.33 | −0.53 | 0.56 |
| LT22.1 | 0.75 | 0.00 | 0.67 | 0.14 | 0.13 | −0.16 | 0.22 |
| S.D. | 0.17 | Failed | 0.03 | 0.06 | 0.18 | 0.13 | 0.17 |

Table 8 indicates the ΔCt values for results of epicenter mapping relative to DNA58125 in lung tumors, indicating the relative amplification in the region more immediate to the actual location of DNA58125 along chromosome 16.

TABLE 8

Amplification of Epicenter Markers Relative to DNA58125 in Colon Tumors

| | P89 | P90 | P92 | P93 | P94 | P95 | DNA58125 |
|---|---|---|---|---|---|---|---|
| Panel 1 | | | | | | | |
| ColT2 | 0.17 | 0.00 | 0.18 | 0.41 | 0.17 | 0.05 | 1.07 |
| ColT3 | −0.73 | 0.00 | −0.50 | −1.04 | 0.21 | −0.61 | 0.66 |
| ColT8 | 0.54 | 0.00 | 0.59 | 0.76 | 0.46 | 0.52 | 2.27 |
| ColT10 | 0.46 | 0.00 | 0.29 | 0.32 | 0.46 | 0.12 | 1.50 |
| ColT12 | 0.09 | 0.00 | −0.15 | 0.05 | 0.57 | 0.01 | 0.81 |
| ColT14 | 0.37 | 0.00 | 0.22 | −0.84 | 0.50 | 0.43 | 0.47 |
| ColT16 | 0.50 | 0.00 | 0.14 | 0.15 | 0.64 | 0.08 | 2.24 |
| ColT17 | 0.15 | 0.00 | 0.26 | −0.42 | 0.07 | −0.02 | 0.82 |
| S.D. | 0.01 | Failed | 0.06 | 0.02 | 0.06 | 0.12 | 0.04 |
| Panel 2 | | | | | | | |
| ColT2 | 0.40 | 0.00 | 0.22 | 0.33 | 0.21 | 0.68 | 2.29 |
| ColT4 | −0.20 | 0.00 | −0.21 | 0.81 | 0.13 | −0.07 | 1.49 |
| ColT5 | 0.25 | 0.00 | 0.17 | −0.30 | 0.14 | −0.12 | 0.71 |
| ColT6 | 0.38 | 0.00 | 0.39 | 0.31 | 0.21 | 0.01 | 1.83 |
| ColT7 | 0.37 | 0.00 | 0.19 | 0.44 | 0.27 | −0.12 | 1.20 |
| ColT9 | 0.53 | 0.00 | 0.47 | 0.52 | 0.20 | 0.20 | 1.67 |
| ColT11 | 0.10 | 0.00 | 0.09 | 0.18 | 0.05 | −0.08 | 1.02 |
| ColT18 | 0.02 | 0.00 | 0.12 | 0.21 | 0.05 | −0.07 | 0.78 |
| S.D. | 0.01 | Failed | 0.08 | 0.25 | 0.06 | 0.02 | 0.10 |

Discussion

The ΔCt(values for DNA58125 (CT-1) in a variety of lung and colon tumors are reported in Tables 2 (initial screen), 4 and 5 (showing amplification by framework analysis relative to markers elsewhere on Chromosome 16), 7 and 8 (showing amplification by epicenter analysis relative to markers in the chromosomal area that DNA58125 is located), as well as in FIGS. 3–12. A ΔCt value >1 (values with a single underline) was typically used as the threshold value for amplification scoring, as this represents a doubling of the gene copy. Table 4 indicates that significant amplification of DNA58125 occurred in primary lung tumors LT3, LT12, LT13, LT15, LTl17, and LT18. The average ΔCt values were 1.02, 1.00, 1.33, 1.83, 1.03, 1.08, respectively, for the lung tumors. This represents approximately a 2.0, 2.0, 2.5, 3.6, 2.0, and 2.1 fold increase, respectively, in gene copy for the lung tumors relative to normal tissue.

Table 5 indicates that significant amplification of DNA58125 occurred in primary colon tumors ColT2, ColT3, ColT8, ColT10, ColT12, ColT14, ColT15, ColT1, ColT4, ColT5, ColT6, ColT11 and ColT18. The average ΔCt values were 2.27, 1.34, 1.23, 1.74, 1.13, 1.74, 1.30, 1.08, 1.13, 2.17, 1.41, 2.24 and 1.04, respectively for the colon tumors. This represents approximately a 4.8, 2.5, 2.3, 3.3, 2.2, 3.3, 2.5, 2.1, 2.2, 4.5, 2.6, 4.7 and 2.0 fold increase in gene copy, respectively, for the colon tumors relative to normal tissue.

In contrast, the amplification of the closest known markers (Tables 7 and 8) are not amplified to a greater extent than DNA58125. Amplification of the closest markers to DNA58125 does not occur to a greater extent than that of DNA58125. This strongly suggests that DNA58125 is the gene that is the cause for the amplification of the particular region on Chromosome 16.

Because amplification of DNA58125 (CT-1) occurs in various tumors, it is likely to play a significant role in tumor formation or growth. As a result, antagonists (e.g., antibodies) directed against the protein encoded by DNA58125 (CT-1) would be expected to be useful in cancer therapy.

Example 2

In situ Hybridization

In situ hybridization is a powerful and versatile technique for the detection and localization of nucleic acid sequences within cell or tissue preparations. It may be useful, for example, to identify sites of gene expression, analyze the tissue distribution of transcription, identify and localize viral infection, follow changes in specific mRNA synthesis and aid in chromosome mapping.

Studies of tissue distribution of cardiotrophin-1 in human tissue was assessed in related U.S. application Ser. No. 08/286,304 filed Aug. 5, 1994, now U.S. Pat. No. 5,571,893 issued Nov. 5, 1996, herein incorporated by reference in its entirety. Such studies are also described by Pennica, D. et al in Cytokine 8(3):183–9 (1996), herein incorporated by reference in its entirety. Poly (A)$^+$RNA from several adult human tissues was screened using a probe from mouse CT-1 cDNA clones. Blot hybridization with a 180 bp mouse CT-1 probe (extending from 19 bp 5' of the initiating ATG through amino acid 50) in 20% formamide, 5×SSC at 42° C. with a final wash at 0.25×SSC at 52° C. A 1.7 kb CT-1 mRNA was shown to be expressed in adult human heart, skeletal muscle, ovary, colon, prostate and testis and in fetal kidney and lung.

In situ hybridization may also be performed following an optimized version of the protocol by Lu and Gillett, *Cell Vision* 1: 169–176 (1994), using PCR-generated $^{33}$P-labeled riboprobes. Briefly, formalin-fixed, paraffin-embedded human tissues are sectioned, deparaffinized, deproteinated in proteinase K (20 g/ml) for 15 minutes at 37° C., and further processed for in situ hybridization as described by Lu and Gillett, supra. A [$^{33}$–P] UTP-labeled antisense riboprobe iss generated from a PCR product and hybridized at 55° C. overnight. The slides are dipped in Kodak NTB2 nuclear track emulsion and exposed for 4 weeks.

$^{33}$P-Riboprobe synthesis 6.0 μl (125 mCi) of $^{33}$P-UTP (Amersham BF 1002, SA<2000 Ci/mmol) were speed vac dried.

To each tube containing dried $^{33}$P-UTP, the following ingredients were added:

2.0 μl 5× transcription buffer
1.0 μl DTT (100 mM)
2.0 μl NTP mix (2.5 mM: 10 μl; each of 10 mM GTP, CTP & ATP+10 μl H$_2$O)
1.0 μl UTP (50 μM)
1.0 μl Rnasin
1.0 μl DNA template (1 μg)
1.0 μl H$_2$O
1.0 μl RNA polymerase (for PCR products T3=AS, T7=S, usually)

The tubes were incubated at 37° C. for one hour. 1.0 μl RQ1 DNase were added, followed by incubation at 37° C. for 15 minutes. 90 μl TE (10 mM Tris pH 7.6/1 mM EDTA pH 8.0) were added, and the mixture was pipetted onto DE81 paper. The remaining solution was loaded in a Microcon-50 ultrafiltration unit, and spun using program 10 (6 minutes). The filtration unit was inverted over a second tube and spun using program 2 (3 minutes). After the final recovery spin, 100 μl TE were added. 1 μl of the final product was pipetted on DE81 paper and counted in 6 ml of Biofluor II.

The probe was run on a TBE/urea gel. 1–3 μl of the probe or 5 μl of RNA Mrk III were added to 3 μl of loading buffer. After heating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in –70° C. freezer one hour to overnight.

$^{33}$P-Hybridization

Pretreatment of frozen sections

The slides were removed from the freezer, placed on aluminum trays and thawed at room temperature for 5 minutes. The trays were placed in 55° C. incubator for five minutes to reduce condensation The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 μg/ml proteinase K for 10 minutes at 37° C. (12.5 μl of 10 mg/ml stock in 250 ml prewarmed RNAse-free RNAse buffer), the sections were washed in 0.5×SSC for 10 minutes at room temperature. The sections were dehydrated in 70%, 95%, 100% ethanol, 2 minutes each.

Pretreatment of paraffin-embedded sections

The slides were deparaffinized, placed in SQ H$_2$O, and rinsed twice in 2×SSC at room temperature, for 5 minutes each time. The sections were deproteinated in 20 μg/ml proteinase K (500 μl of 10 mg/ml in 250 ml RNase-free RNase buffer; 37° C., 15 minutes )-human embryo, or 8×proteinase K (100 μl in 250 ml Rnase buffer, 37° C., 30 minutes)-formalin tissues. Subsequent rinsing in 0.5×SSC and dehydration were performed as described above.

Prehybridization

The slides were laid out in plastic box lined with Box buffer (4×SSC, 50% formamide)-saturated filter paper. The tissue was covered with 50 μl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1–4 hours.

Hybridization 1.0×10$_6$ cpm probe and 1.0 μl tRNA (50 mg/ml stock) per slide were heated at 95° C. for 3 minutes. The slides were cooled on ice, and 48 μl hybridization buffer were added per slide. After vortexing, 50 μl $^{33}$P mix were added to 50 μl prehybridization on slide. The slides were incubated overnight at 55° C.

Washes

Washing was done 2×10 minutes with 2×SSC, EDTA at room temperature (400 ml 20×SSC+16 ml 0.25M EDTA, V$_1$=4L), followed by RNaseA treatment at 37° C. for 30 minutes (500 μl of 10 mg/ml in 250 ml Rnase buffer=20 μg/ml). The slides were washed 2×10 minutes with 2×SSC, EDTA at room temperature. The stringency wash conditions were as follows: 2 hours at 55° C., 0.1×SSC, EDTA (20×ml 20×SSC+16 ml EDTA, V$_1$=4L).

Example 3

Use of CT-1 as a hybridization probe

The following method describes use of a nucleotide sequence encoding a CT-1 polypeptide as a hybridization probe.

DNA comprising the coding sequence of full-length or mature CT-1 (as shown in FIG. 1A, SEQ ID NO:1 and 2) is employed as a probe to screen for homologous DNAs (such as those encoding naturally-occurring variants of CT-1) in human tissue cDNA libraries or human tissue genomic libraries.

Hybridization and washing of filters containing either library DNAs is performed under the following high stringency conditions. Hybridization of radiolabeled CT-1-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence CT-1 can then be identified using standard techniques known in the art.

Example 4

Expression of CT-1 in E. coli

This example illustrates preparation of an unglycosylated form of CT-1 by recombinant expression in E. coli.

The DNA sequence encoding CT-1 (SEQ ID NO:1) is initially amplified using selected PCR primers. The primers should contain restriction enzyme sites which correspond to the restriction enzyme sites on the selected expression vector. A variety of expression vectors may be employed. An example of a suitable vector is pBR322 (derived from E. coli; see Bolivar et al., Gene, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyhis leader (including the first six STII codons, polyhis sequence, and enterokinase cleavage site), the CT-1 coding region, lambda transcriptional terminator, and an argU gene.

The ligation mixture is then used to transform a selected E. coli strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized CT-1 protein can then be purified using a metal chelating column under conditions that allow tight binding of the protein.

CT-1 is expressed in E. coli in a poly-His tagged form, using the following procedure. The DNA encoding CT-1 is initially amplified using selected PCR primers. The primers contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an E. coli host based on strain 52 (W3110 fuhA (tonA) lon galE rpoHts(htpRts) clpP(lacIq). Transformants are first grown in LB containing 50 mg/ml carbenicillin at 30° C. with shaking until an O.D.600 of 3–5 is reached. Cultures were then diluted 50–100 fold into CRAP media (prepared by mixing 3.57 g $(NH_4)_2SO_4$, 0.71 g sodium citrate.2H2O, 1.07 g KCl, 5.36 g Difco yeast extract, 5.36 Sheffield hycase SF in 500 mL water, as well as 110 mM MPOS, pH 7.3, 0.55% (w/v) glucose and 7 mM $MgSO_4$) and grown for approximately 20–30 hours at 30° C. with shaking. Samples are removed to verify expression by SDS-PAGE analysis, and the bulk culture is centrifuged to pellet the cells. Cell pellets are frozen until purification and refolding.

E. coli paste from 0.5 to 1 L fermentations (6–10 g pellets) is resuspended in 10 volumes (w/v) in 7 M guanidine, 20 mM Tris, pH 8 buffer. Solid sodium sulfite and sodium tetrathionate is added to make final concentrations of 0.1M and 0.02M, respectively, and the solution was stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3–5 volumes of metal chelate column buffer (6 M guanidine, 20 mM Tris, pH 7.4) and filtered through 0.22 micron filters to clarify. Depending the clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12–36 hours. The refolding reaction is quenched by the addition of TFA to a final concentration of 0.4% (pH of approximately 3). Before further purification of the protein, the solution is filtered throuh a 0.22 micron filter and acetonitrile is added to 2–10% final concentration. The refolded protein is chromatographed on a Poros R1/H reversed phase column using a mobile buffer of 0.1% TFA with elution with a gradient of acetonitrile from 10 to 80%. Aliquots of fractions with $A_{280}$ absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species arc usually eluted at higher acetonitrile concentrations. In addition to resolving misfolded forms of proteins from the desired form, the reversed phase step also removes endotoxin from the samples.

Fractions containing the desired folded CT-1 proteins, respectively, are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 5

Expression of CT-1 in mammalian cells

This example illustrates preparation of a glycosylated form of CT-1 by recombinant expression in mammalian cells.

The vector, pRK5 (see EP 307,247, published Mar. 15, 1989), is employed as the expression vector. Optionally, the CT-1 DNA is ligated into pRK5 with selected restriction enzymes to allow insertion of the CT-1 DNA using ligation methods such as described in Sambrook et al., supra. The resulting vector is called pRK5-CT-1.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-CT-1 DNA is mixed with about 1 µg DNA encoding the VA RNA gene [Thimmappaya et al., Cell, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added lo the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysteine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of CT-1 polypeptide. The cultures containing transfected cells may undergo further incubation (in serum free medium) and the medium is tested in selected bioassays.

In an alternative technique, CT-1 DNA may be introduced into 293 cells transiently using the dextran sulfate method described by Somparyrac et al., Proc. Natl. Acad. Sci., 12:7575 (1981). 293 cells are grown to maximal density in a spinner flask and 700 µg pRK5-CT-1 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed CT-1 can then be concentrated and purified by any selected method, such as dialysis and/or column chromatography.

In another embodiment, CT-1 can be expressed in CHO cells. The pRK5-CT-1 vector can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of CT-1 polypeptide, the culture medium may be replaced with serum free medium. Preferably, the cultures are incubated for about 6 days, and then the conditioned medium is harvested. The medium containing the expressed CT-1 can then be concentrated and purified by any selected method.

Epitope-tagged CT-12 may also be expressed in host CHO cells. The CT-1 may be subcloned out of the pRK5 vector. The subclone insert can undergo PCR to fuse in frame with a selected epitope tag such as a poly-His tag into a Baculovirus expression vector. The poly-His tagged CT-1 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged CT-1 can then be concentrated (and purified by any selected method, such as by $Ni^2$-chelate affinity chromatography.

CT-1 was expressed in CHO cells by both a transient and a stable expression procedure. Stable expression in CHO cells was performed using the following procedure. The proteins were expressed as an IgG construct (immunoadhesin), in which the coding sequences for the soluble forms (e.g. extracellular domains) of the respective proteins were fused to an IgG1 constant region sequence containing the hinge, CH2 and CH2 domains and/or is a poly-His tagged form.

Following PCR amplification, the DNA58125 is subcloned in a CHO expression vector using standard techniques as described in Ausubel et al., Current Protocols of Molecular Biology, Unit 3.16, John Wiley and Sons (1997). CHO expression vectors are constructed to have compatible restriction sites 5' and 3' of the DNA of interest to allow the convenient shuttling of cDNA's. The vector uses expression in CHO cells is as described in Lucas et al, Nucl. Acids Res. 24: 9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA were introduced into approximately 10 million CHO cells using commercially available transfection reagents Superfect® (Quiagen), Dosper® or Fugene® (Boehringer Mannheim). The cells were grown and described in Lucas et al., supra. Approximately $3 \times 10^{-7}$ cells are frozen in an ampule for further growth and production as described below.

The ampules containing the plasmid DNA were thawed by placement into a water bath and mixed by vortexing. The contents were pipetted into a centrifuge tube containing 10 mLs of media and centrifuged at 1000 rpm for 5 minutes. The supernatant was aspirated and the cells were resuspended in 10 mL of selective media (0.2 µm filtered PS20 with 5% 0.2 µm diafiltered fetal bovine serum). The cells were then aliquoted into a 100 mL spinner containing 90 mL of selective media. After 1–2 days, the cells were transferred into a 250 mL spinner filled with 150 mL selective growth medium and incubated at 37° C. After another 2–3 days, a 250 mL, 500 mL and 2000 mL spinners were seeded with $3 \times 10^5$ cells/mL. The cell media was exchanged with fresh media by centrifugation and resuspension in production medium. Although any suitable CHO media may be employed, a production medium described in U.S. Pat. No. 5,122,469, issued Jun. 16, 1992 was actually used. 3L production spinner is seeded at $1.2 \times 10^6$ cells/mL. On day 0, the cell number pH were determined. On day 1, the spinner was sampled and sparging with filtered air was commenced. On day 2, the spinner was sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion). Throughout the production, pH was adjusted as necessary to maintain a pH of about 7.2. After 10 days, or until viability dropped below 70%, the cell culture was harvested by centrifugtion and filtering through a 0.22 µm filter. The filtrate was either stored at 4° C. or immediately loaded onto columns for purification.

For the poly-His tagged constructs, the proteins were purified using a Ni-NTA column (Qiagen). Before purification, imidazole was added to the conditioned media to a concentration of 5 mM. The conditioned media was pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M imidazole. The highly purified protein as subsequently desalted into a storage buffer containing 10 mM Hepes, 0.14 M NaCl and 4% mannitol, pH 6.8, with a 25 ml G25 Superfine (Pharmacia) column and stored at −80° C.

CT-1 may be produced by transient expression in COS cells, as well, using standard techniques.

EXAMPLE 6

Expression of CT-1 in Yeast

The following method describes recombinant expression of CT-1 in yeast.

First, yeast expression vectors are constructed for intracellular production or secretion of CT-1 from the ADH2/GAPDH promoter. DNA58125 encoding CT-1 and the promoter is inserted into suitable restriction enzyme sites in the selected plasmid to direct intracellular expression of CT-1. For secretion, DNA encoding CT-1 can be cloned into the selected plasmid, together with DNA encoding the ADH2/GAPDH promoter, a native CT-1 signal peptide or other mammalian signal peptide, or, for example, a yeast alpha-factor or invertase secretory signal/leader sequence, and linker sequences (if needed) for expression of CT-1.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant CT-1 can subsequently be isolated and purified by removing the yeast cells from the fermentation medium by centrifugation and then concentrating the medium using selected cartridge filters. The concentrate containing CT-1 may further be purified using selected column chromatography resins.

EXAMPLE 7

Expression of CT-1 in Baculovirus-Infected Insect Cells

The following method describes recombinant CT-1 expression in Baculovirus-infected insect cells.

The sequence coding for CT-1 is fused upstream of an epitope tag contained within a baculovirus expression vector. Such epitope tags include poly-His tags and immunoglobulin tags (like Fc regions of IgG). A variety of plasmids may be employed, including plasmids derived from commercially available plasmids such as pVLI 393 (Novagen). Briefly, the sequence encoding CT-1 or the desired portion of the coding sequence of CT-1 (such as the sequence encoding the extracellular domain of a transmembrane protein or the sequence encoding the mature protein if the protein is extracellular) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCCCRL 1711) using lipofectin (commercially available from GIBCO-BRL). After 4–5 days of incubation at 28° C., the released viruses are harvested and used for further amplifications. Viral infection and protein expression are performed as described by O'Reilley et al., *Baculovirus expression vectors: A Laboratory Manual,* Oxford: Oxford University Press (1994). Expressed poly-His tagged CT-1 can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphates 300 mM NaCl, 10% glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes non-specifically bound portein. After reaching $A_{280}$ baseline again, the column is developed with a 0 to 500 mM imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted His $_{10}$-tagged CT-1 are pooled and dialyzed against loading buffer. Alternatively, purification of the IgG tagged (or Fe tagged) CT-1 can be performed using known chromatography techniques, including for instance, Protein A or Protein G column chromatography.

While the CT-1 expression is performed in a 0.5–2L scale, it can be readily scaled up for larger (e.g. 8L) preparations. CT-1 is also expressed as an IgG construct (immunoadhesin), in which the protein extracellular region is fused to an $IgG_1$ constant region sequence containing the hinge, CH2 and CH3 domains and/or in poly-His tagged forms.

Following PCR amplification, the coding sequence is subcloned into a baculovirus expression vector (pb.PH.IgG for IgG fusions and pb.PH.His.c for poly-His tagged proteins), and the vector and Baculogold® baculovirus DNA(Pharmingen) is co-transfected into 105 *Spondoptera frugiperda* ("Sf9") cells (ATCC CRL 1711), using Lipofectin (Gibco BRL). pb.PH.IgG and pb.PH.His are modifications of the commercially available baculovirus expression vector pVL1393 (Pharmingen), with modified polylinker regions to include the His or Fc tag sequences. The cells are grown in Hink's TNM-FH medium supplemented with 10% FBS (Hyclone). Cells are incubated for 5 days at 28° C. The supernatant is harvested and subsequently used for the first viral amplification by infecting Sf9 cells in Hink's TNM-FH medium supplemented with 10% FBS at an approximate multiplicity of infection (MOI) of 10. Cells are incubated for 3 days at 28° C. The supernatant is harvested and the expression of the constructs in the baculovirus expression vector is determined by batch binding of 1 mL of supernatant to 25 mL of of NI-NTA beads (Qiagen) for histidine tagged proteins or Protein-A Sepharose CL-4B beads (Pharmacia) for IgG tagged proteins followed by SDS-PAGE analysis comparing to a known concentration of protein standard by Coomassie blue staining.

The first viral amplification supernatant is used to infect a spinner culture (500 mL) of Sf9 cells grown in ESF-921 medium (Expression Systems LLC) at an approximate MOI of 0.1. Cells are incubated for 3 days at 28° C. The supernatant is harvested and filtered. Batch binding and SDS-PAGE analysis is repeated, as necessary, until expression of the spinner culture is confirmed.

The conditioned medium from the transfected cells (0.5 to 3 L) is harvested by centrifugation to remove the cells and filtered through 0.22 micron filters. For the poly-His taged constructs, the protein construct are purified using a Ni-NTA column (Qiagen). Before purification, imidazole is added to the conditioned media to a concentration of 5 mM. The conditioned media are pumped onto a 6 mL Ni-NTA column equilibrated in 20 mM Hepes, pH 7.4 buffer containing 0.3 M NaCl and 5 mM imidazole at a flow rate of 4–5 mL/min. at 4° C. After loading the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 mL G25 Superfine (Pharmacia) column and stored at −80° C.

Immunoadhesin (Fc containing) constructs of proteins are purified from the conditioned medium as follows. The conditioned medium is pumped onto a 5 mL Protein A column (Pharmacia) which had been equilibrated in 20 mM sodium phosphate buffer, pH 6.8. After loading, the column is washed extensively with equilibration buffer before elution with 100 mM citric acid, pH 3.5. The eluted protein is immediately neutralized by collecting 1 mL fractions into tubes containing 275 of 1 M Tris buffer, pH 9. The highly purified protein is subsequently desalted into storage buffer as described above for the poly-His tagged proteins. The homogeneity of the proteins is verified by SDS-PAGE and N-terminal amino acid sequencing by Edman degradation.

EXAMPLE 8

Preparation of Antibodies that Bind CT-1

This example illustrates preparation of monoclonal antibodies which can specifically bind CT-1.

Techniques for producing the monoclonal antibodies are known in the art and are described, for instance, in Goding, supra. Immunogens that may be employed include purified CT-1, fusion proteins containing CT-1, and cells expressing recombinant CT-1 on the cell surface. Selection of the immunogen can be made by the skilled artisan without undue experimentation.

Mice, such as BAlb/c, are immunized with the CT-1 immunogen emulsified incomplete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, MT) and injected into the animal's hind foot pads. The immunized mice are then boosted 10 to 12 days later with additional immunogen emulsified in the selected adjuvant. Thereafter, for several weeks, the mice may also he boosted with additional immunization injections. Serum samples may be periodically obtained from the mice by retro-orbital bleeding for testing in ELISA assays to detect anti-CT-1 antibodies.

After a suitable antibody titer has been detected, the animals "positive" for antibodies can be injected with a final intravenous injection of CT-1. Three to four days later, the mice are sacrificed and the spleen cells are harvested. The, spleen cells are then fused (using 35% polyethyleene glycol) to a selected murine myeloma cell line such as P3x63AgU0.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells are screened in an ELISA for reactivity against CT-1. Determination of "positive" hybridoma cells secreting the desired monoclonal antibodies against CT-1 is within the skill in the art.

The positive hybridoma cells can be injected intraperitoneally into syngeneic Balb/c mice to produce ascites containing the anti-CT-1 monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to Protein A or Protein G can be employed.

Deposit of Material

The following material, a plasmid encoding CT-1 (disclosed in U.S. Ser. No. 08/286,304 filed Aug. 5, 1994, now U.S. Pat. No. 5,571,893, issued Nov. 5, 1996), has been deposited with the American Type Culture Culture Collection, 10801 University Blvd., Manassas, Va. 20110–2209, USA (ATCC):

| Material | ATCC Dep. No. | Deposit Date |
|---|---|---|
| pBSSK + .huCT1.h5 | 75,841 | July 26, 1994 |

This deposit was made under the provisions of the Budapest Treaty on the International Recognition of the Deposit of Microorganisms for the purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The foregoing written specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the this invention. The deposit of material herein does not constitute an admission that the written description herein contained is inadequate to enable the practice of any aspect of the invention, including the best mode thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. A mouse comprising homologously recombined DNA wherein the cardiotrophin-1 (CT-1) gene is altered such that CT-1 polypeptide is non-functional or absent.

2. The mouse of claim 1 wherein the mouse is characterized by decreased neuronal survival.

* * * * *

SEQUENCE LISTING

<160> NUMBER OF SEQ ID NOS: 6

<210> SEQ ID NO 1
<211> LENGTH: 1539
<212> TYPE: DNA
<213> ORGANISM: Human

<400> SEQUENCE: 1

```
gtgaagggag ccgggatcag ccagggca gcatgagccg gagggaggga              50
agtctggaag accccagac tgattcctca gtctcacttc ttccccactt             100
ggaggccaag atccgtcaga cacacagcct tgcgcacctc ctcaccaaat            150
acgctgagca gctgctccag gaatatgtgc agctccaggg agacccccttc           200
gggctgccca gcttctcgcc gccgcggctg ccggtggccg gcctgagcgc            250
cccggctccg agccacgcgg ggctgccagt gcacgagcgg ctgcggctgg            300
acgcggcggc gctggccgcg ctgccccgc tgctggacgc agtgtgtcgc             350
cgccaggccg agctgaaccc gcgcgcgccg cgcctgctgc gccgcctgga            400
ggacgcggcg cgccaggccc gggccctggg cgccgccgtg gaggccttgc            450
tggccgcgct gggcgccgcc aaccgcgggc cccggccga gccccccgcc             500
gccaccgcct cagccgcctc cgccaccggg gtcttccccg ccaaggtgct            550
ggggctccgc gtttgcggcc tctaccgcga gtggctgagc cgcaccgagg            600
gcgacctggg ccagctgctg cccggggggct cggcctgagc gccgcgggc            650
agctcgcccc gcctcctccc gctgggttcc gtctctcctt ccgcttcttt            700
gtctttctct gccgctgtcg gtgtctgtct gtctgctctt agctgtctcc            750
attgcctcgg ccttctttgc tttttgtggg ggagagggga ggggacgggc            800
agggtctctg tcgcccaggc tggggtgcag tggcgcgatc ccagcactgc            850
agcctcaacc tcctgggctc aagccatcct tccgcctcag cttccccagc            900
agctgggact acaggcacgc gccaccacag ccggctaatt ttttatttaa            950
ttttttgtag agacgaggtt tcgccatgtt gcccaggctg gtcttgaact            1000
ccggggctca agcgatcctc ccgcttcagc ctccctaagt gctgggattg            1050
caggcgtgag ccactttccc agcctctctt tgctttgcct gccccgttct            1100
cttaactctt ggaccctcct cgtctgcatg gtaactccgt ctgagtctac            1150
cattttcttg ctctccctcc ttccttgggc ctgcctcagt tccctttggc            1200
ctcccccttt acccagctct tggggtgtct ctgttttttc catccccact            1250
tcctgccttc tcgtggccct gtggtagcac atgtgtacat ctcagcctta            1300
tctcaaggag gtgacaccttt ctctccttgt ccccatctgg ccgtctctct           1350
gtgcttccct ggccagggc gtgcctgctg gtcctatggg gggaaggcta             1400
ctccgcatct cagccacctt cctcaggctc actccaccta catccccagt            1450
```

-continued

| | |
|---|---|
| ctgccacacc ccatcccttt gggcctcagc cctgtcccttt tgatgtcctc | 1500 |
| ctttccttca gcccctctgc cctgtccctg cacacctcc | 1539 |

<210> SEQ ID NO 2
<211> LENGTH: 1539
<212> TYPE: DNA
<213> ORGANISM: Human

<400> SEQUENCE: 2

| | |
|---|---|
| ggaggtgtgc agggacaggg cagagggct gaaggaaagg aggacatcaa | 50 |
| agggacaggg ctgaggccca aagggatggg gtgtggcaga ctggggatgt | 100 |
| aggtggagtg agcctgagga agtggctga gatgcggagt agccttcccc | 150 |
| ccataggacc agcaggcacg cccctggcca gggaagcaca gagagacggc | 200 |
| cagatgggga caaggagaga aggtgtcacc tccttgagat aaggctgaga | 250 |
| tgtacacatg tgctaccaca gggccacgag aaggcaggaa gtgggatgg | 300 |
| aaaaaacaga dacaccccaa gagctgggta aaggggagg ccaaagggaa | 350 |
| ctgaggcagg cccaaggaag gagggagagc aagaaaatgg tagactcaga | 400 |
| cggagttacc atgcagacga ggagggtcca agagttaaga gaacgggca | 450 |
| ggcaaagcaa agagaggctg ggaaagtggc tcacgcctgc aatcccagca | 500 |
| cttaggagg ctgaagcggg aggatcgctt gagccccgga gttcaagacc | 550 |
| agcctgggca acatggcgaa acctcgtctc tacaaaaaat taaataaaaa | 600 |
| attagccggc tgtggtggcg cgtgcctgta gtcccagctg ctgggaagc | 650 |
| tgaggcggaa ggatggcttg agcccaggag gttgaggctg cagtgctggg | 700 |
| atcgcgccac tgcaccccag cctgggcgac agagaccctg cccgtcccct | 750 |
| cccctctccc ccacaaaaag caaagaaggc cgaggcaatg gagacagcta | 800 |
| agagcagaca gacagacacc gacagcggca gagaaagaca aagaagcgga | 850 |
| aggagagacg gaacccagcg ggaggaggcg gggcgagctg ccccgcggcg | 900 |
| ctcaggccga gccccgggc agcagctggc ccaggtcgcc ctcggtgcgg | 950 |
| ctcagccact cgcggtagag gccgcaaacg cggagcccca gcaccttggc | 1000 |
| ggggaagacc ccggtggcgg aggcggctga ggcggtggcg gcgggggggct | 1050 |
| cggcccgggg cccgcggttg gcggcgccca gcgcggccag caaggcctcc | 1100 |
| acggcggcgc ccagggcccg ggcctggcgc gccgcgtcct ccaggcggcg | 1150 |
| cagcaggcgc ggcgcgcgcg ggttcagctc ggcctggcgg cgacacactg | 1200 |
| cgtccagcag cggggcagc gcggccagcg ccgccgcgtc cagccgcagc | 1250 |
| cgctcgtgca ctggcagccc cgcgtggctc ggagccgggg cgctcaggcc | 1300 |
| ggccaccggc agccgcggcg gcgagaagct gggcagcccg aagggtctc | 1350 |
| cctggagctg cacatattcc tggagcagct gctcagcgta tttggtgagg | 1400 |
| aggtgcgcaa ggctgtgtgt ctgacggatc ttggcctcca agtggggaag | 1450 |
| aagtgagact gaggaatcag tctgggggtc ttccagactt ccctccctcc | 1500 |
| ggctcatgct ggcccctggc tgatcccggc tcccttcac | 1539 |

<210> SEQ ID NO 3
<211> LENGTH: 201
<212> TYPE: PRT
<213> ORGANISM: Human

```
<400> SEQUENCE: 3

Met Ser Arg Arg Glu Gly Ser Leu Glu Asp Pro Gln Thr Asp Ser
 1               5                  10                  15

Ser Val Ser Leu Leu Pro His Leu Glu Ala Lys Ile Arg Gln Thr
                20                  25                  30

His Ser Leu Ala His Leu Leu Thr Lys Tyr Ala Glu Gln Leu Leu
                35                  40                  45

Gln Glu Tyr Val Gln Leu Gln Gly Asp Pro Phe Gly Leu Pro Ser
                50                  55                  60

Phe Ser Pro Pro Arg Leu Pro Val Ala Gly Leu Ser Ala Pro Ala
                65                  70                  75

Pro Ser His Ala Gly Leu Pro Val His Glu Arg Leu Arg Leu Asp
                80                  85                  90

Ala Ala Ala Leu Ala Ala Leu Pro Pro Leu Leu Asp Ala Val Cys
                95                 100                 105

Arg Arg Gln Ala Glu Leu Asn Pro Arg Ala Pro Arg Leu Leu Arg
               110                 115                 120

Arg Leu Glu Asp Ala Ala Arg Gln Ala Arg Ala Leu Gly Ala Ala
               125                 130                 135

Val Glu Ala Leu Leu Ala Ala Leu Gly Ala Ala Asn Arg Gly Pro
               140                 145                 150

Arg Ala Glu Pro Pro Ala Ala Thr Ala Ser Ala Ala Ser Ala Thr
               155                 160                 165

Gly Val Phe Pro Ala Lys Val Leu Gly Leu Arg Val Cys Gly Leu
               170                 175                 180

Tyr Arg Glu Trp Leu Ser Arg Thr Glu Gly Asp Leu Gly Gln Leu
               185                 190                 195

Leu Pro Gly Gly Ser Ala
               200

<210> SEQ ID NO 4
<211> LENGTH: 21
<212> TYPE: DNA
<213> ORGANISM: Human

<400> SEQUENCE: 4
ttcccagcct ctctttgctt t                                          21

<210> SEQ ID NO 5
<211> LENGTH: 22
<212> TYPE: DNA
<213> ORGANISM: Human

<400> SEQUENCE: 5
tcagacggag ttaccatgca ga                                         22

<210> SEQ ID NO 6
<211> LENGTH: 27
<212> TYPE: DNA
<213> ORGANISM: Human

<400> SEQUENCE: 6
tgccccgttc tcttaactct tggaccc                                    27
```